United States Patent
Meyer et al.

(10) Patent No.: US 6,280,760 B1
(45) Date of Patent: Aug. 28, 2001

(54) PEPTIDE-COATED IMPLANTS AND METHODS FOR PRODUCING SAME

(75) Inventors: Jorg Meyer, Egelsbach; Alfred Jonczyk, Darmstadt; Berthold Nies, Frankisch-Crumbach; Horst Kessler; Dirk Finsinger, both of Garching; Martin Kantlehner, Freising, all of (DE)

(73) Assignee: Merck Patent Gesellschaft mit beschraenkter Haftung, Darmstadt (DE)

( * ) Notice: Subject to any disclaimer, the term of this patent is extended or adjusted under 35 U.S.C. 154(b) by 0 days.

(21) Appl. No.: 09/423,347
(22) PCT Filed: May 9, 1998
(86) PCT No.: PCT/EP98/02753
§ 371 Date: Nov. 22, 1999
§ 102(e) Date: Nov. 22, 1999
(87) PCT Pub. No.: WO98/52619
PCT Pub. Date: Nov. 26, 1998

(30) Foreign Application Priority Data

| May 22, 1997 | (DE) | 197 21 352 |
| Dec. 16, 1997 | (DE) | 197 55 801 |
| Apr. 23, 1998 | (DE) | 198 18 098 |

(51) Int. Cl.[7] .................. A61L 27/00; C07K 17/06
(52) U.S. Cl. .......... 424/423; 424/422; 623/1.49; 623/2.42; 623/3.29; 623/8; 623/11

(58) Field of Search ................ 623/1, 2, 3, 8, 623/11, 12, 16, 18, 22, 23, 1.49, 2.42, 3.29; 435/1.1; 424/422, 423

(56) References Cited

U.S. PATENT DOCUMENTS

| 5,554,594 | * | 9/1996 | Zoller et al. ............... 514/18 |
| 5,641,644 | * | 6/1997 | Klebe ....................... 435/30 |
| 5,906,828 | * | 5/1999 | Cima et al. ................. 424/423 |

FOREIGN PATENT DOCUMENTS 92 00047    1/1992 (WO).

OTHER PUBLICATIONS

HIRANO Y. et al., "Synthesis and cell attachnent activity of bioactive oligopeptides . . . ," *Journal of Biomedical Materials Research*, vol. 25, No. 12, Dec. 1991, pp. 1523–1534.
International Search Report for PCT/EP98/02753 mailed Feb. 1, 1999.
Cheng et al. The Integrin Complex $\alpha_v\beta_3$ Participates . . . Exp. Cell Research. vol. 194, pp. 69–77, 1991.*

* cited by examiner

Primary Examiner—Jeffrey E. Russel
(74) Attorney, Agent, or Firm—Millen, White, Zelano & Branigan, P.C.

(57) ABSTRACT

The invention describes the possibility of the biofunctionalization of biomaterials, in particular implants, by their made-to-measure coating with synthesized cell- or tissue-selective RGD peptides which in vitro stimulate the adhesion of mainly those cell species which in each case are intended to accomplish the tissue integration of the appropriate biomaterial.

21 Claims, 17 Drawing Sheets

PEPTIDE-COATED IMPLANTS AND METHODS FOR PRODUCING SAME

The invention relates to implants of a general nature for the human and animal body, which are coated with peptides which are able to selectively mediate the adhesion of specific cells in the particular environment of the implant. In particular, the invention relates to implants coated with RGD peptides and processes for their preparation.

The invention is based on the principle of targeted adhesion stimulation of selected cell species to surface coatings of biomaterials in general and implants in particular for the purpose of tissue-selective, accelerated and enhanced integration thereof after surgical insertion into the appropriate tissue.

In this manner, various surface parts of an implant can be coated with and made available to various peptides mediating cell adhesion, in particular RGD peptides, which take account of the specific tissue environment into which the implants are inserted.

In this manner, moreover, with respect to tissue engineering the generation of "intelligent" biohybrid organs which carry the biological information for organ regeneration is possible by self-organization by means of specific activation of various cell species by various peptides in different regions of the implant surface.

The term "peptides according to the invention" in the following includes, if not stated otherwise or additionally, all peptides which are able to mediate cell adhesion. Among these, especially those are intended which contain the amino acids arginine (R), glycine (G) and aspartic acid (D) one after the other (RGD peptides). Examples of suitable RGD peptides and suitable peptides not containing RGD are mentioned further below. Furthermore included are corresponding peptides which do not contain the RGD sequence, but nevertheless affect cell adhesion. In the widest sense, the invention also includes non-peptide compounds which qualitatively have the same biological activity as said peptide compounds.

Biomaterials or implants in the sense according to the invention are designated as materials which can be introduced into the human or animal body in order to restore the function of the corresponding functionally damaged natural tissue. These include, for example, hip endoprostheses, artificial knee joints, jaw implants, tendon replacements, skin replacements, vascular prostheses, heart pacemakers, artificial heart valves, breast implants, stents, catheters and shunts.

The integration behaviour of implants in the body still proves problematical. The tissue integration of the materials often proceeds too slowly and too incompletely in order to produce a mechanical stability of the tissue/biomaterial bonding which is adequate for functionality. The composition of the implant surface, which on account of its inadequate interfacial compatibility or biocompatibility prevents an active absorption of surrounding healthy tissue or cells, is often causally responsible for this. This complicates the formation of a stable tissue-implant boundary layer and thus leads to inadequate tissue integration, which in turn results in loosening, tissue resorption, infections, inflammations, allergies, microthrombi formation (restenosis). As a result, revision interventions for the replacement of the implants (e.g. hip endoprostheses, jaw implants, catheters or external fixators) and thus renewed surgical interventions become necessary (Malchau and Herberts, 1996, Prognosis of the Total Hip Arthoplasty, 63. Annual Meeting of the American Academy of Orthopaedic Surgeons, Atlanta; Haddad et al, 1996, The Journal of Bone and Joint Surgery, 78-B:546–549; Collinge et al., 1996, Pin Tract Infections).

Moreover, in particular in the case of hip endoprostheses, so-called aseptic implant loosening proves problematical in which bone cells and thus bony tissue do not, as desired, form the direct connection to the biomaterial, but fibroblasts and connective tissue occur as interfering elements. As a consequence, the prosthesis is lined by connective tissue instead of bony tissue, the resulting stability of the prosthesis-connective tissue bond not being adequate to meet the mechanical demands on the force transmission of an artificial hip joint. As a result, this can lead to loosening of the prosthesis (Pilliar et al., 1986, Clin. Orthop., 208:108–113) and likewise necessitates revision. A further example of undesirable cell types adhering to implants are blood platelets, which can lead to the formation of microthrombi and thus to impaired implant integration (Phillips et al., 1991, Cell 65, 359).

The lack of integrability of biomaterials or implants into the body has a particularly serious effect in the case of complete replacement organs, since here the different cell types come into contact with the implant and the necessary integrability should be targeted. In order to avoid extremely complicated transplantation procedures with the aid of other patients, it is attempted, for example, to accomplish the therapy of functional failure of liver, pancreas, kidney and spleen more and more frequently in the field of tissue engineering by means of so-called biohybrid organs, which consist of carrier materials which are covered with living cells and can be implanted as a functional unit. In most cases, for this purpose functional, healthy cells are included or encapsulated in vitro in resorbable or non-resorbable membranes and transplanted into the patient as artificial biohybrid organs or hollow organs (for example: Lim et al., 1980, Science 210, 908–912; Altman et al., 1982, Horm. Met. Res. Suppl. 12, 43–45; Zekorn et al., 1989, Transplantation Proceedings 21, 2748–2750; Altman et al., 1982, Horm. Met. Res. Suppl. 12, 43–45; EP 0 504 781 B1). However, here too the problems described of the fibrous ensheathing with associated lack of nutrient supply to the transplants, immunological defence reactions due to cell release from the capsules and the formation of blood clots on account of the thrombogenicity of the material surfaces very often occur.

It is known to stimulate the tissue integration of biomaterials/implants by coating thereof with peptides which mediate cell adhesion. For this purpose, on the one hand, those peptides which contain the tripeptide amino acid sequence arginine-glycine-aspartic acid (RGD), or their non-peptide analogues and, on the other hand, cell adhesion-mediating, non-RGD-containing peptides (for examples see below), or their non-peptide analogues, which, as is known, as integral constituents of many proteins, inter alia of the extracellular matrix (e.g. collagen type I, fibronectin, laminin, vitronectin, entactin, osteopontin, thrombospondin) or of the blood clotting cascade (fibrinogen, von Willebrand factor) function as central recognition patterns for the adhesion of eukaryotic cells (e.g.: Pierschbacher and Ruoslahti, 1984; Nature, 309:30–33; Yamada, 1991, J. Biol. Chem., 266:12809–12812). The sequences defined according to the invention are recognized and bound by the respective receptors on the cell surface, the integrins. Since the adhesion of cells to the corresponding proteins is mediated by a large number of different integrins, the integrin expression pattern of a cell species is crucial for their adhesion properties to these proteins. The made-to-measure design and the synthesis of mostly short-chain peptides equipped with the appropriate sequences, which can bind selectively and specifically only to certain integrins, make possible the targeted activation of only those cell species which express these integrins. Thus, for example, RGD peptides are known which bind selectively to alpha$_v$-integrin receptors and thus are preferably able to stimulate the binding (adhesion) of alpha$_v$beta$_3$-/alpha$_v$beta$_5$-bearing cells (osteoblasts, osteoclasts, endothelial cells) without simultaneously being able to stimulate the adhesion of undesirable cell species, e.g. $\alpha_{IIb}\beta_3$-bearing blood platelets (Haubner et al., 1996, 7, Am. Chem. Soc., 118:7461). In contrast, other RGD peptides show a reverse effect and preferably bind to $\alpha_{IIb}\beta_3$-integrin receptors, thus exhibiting selectivity, for example, for blood platelets (Phillips et al., 1991, Cell 65, 359).

The furnishing of implant surfaces with synthetically accessible peptides defined according to the invention is known. In this case, the peptides are attached to the surface to a greater or lesser extent by adsorption or else by covalent bonding. In DE 1 97 06 667, for example, biomaterials are described which relate to bone replacement materials which are based on a porous polymer material which has a surface covering by peptides with an RGD amino acid sequence due to adsorption. In WO 91-05036, metallic prostheses, in particular of titanium or titanium alloys, are furthermore disclosed to whose surfaces peptides, which inter alia can also have RGD sequences, are covalently bonded. Valentini et al. (May 1997, Transactions of the 23rd Annual Meeting of the Society for Biomaterials, New Orleans, USA) describe the covalent binding of RGD peptides to titanium screws provided with a fluorinated ethylenepropylene intermediate layer. Rezania et al. report on the same meeting of silicon dioxide or titanium dioxide surfaces which are coated by means of covalent bonding with amino functional organosilanes and in turn covalently accomplish by means of a heterobifunctional crosslinker the binding of thiol-containing RGD peptides.

These technical solutions, however, do not go into the requirement of making available implants or biomaterials whose surfaces are coated specifically with peptides defined according to the invention, which are selectively tailored to the particular cell type of the tissue surrounding the implant concerned.

It would therefore be desirable to be able to modify biomaterials in such a way that specifically those tissue or cell species which also, after insertion of the implant into the body, should function actively with these, i.e., for example, bone cells in hip endoprostheses or epithelial cells for skin, hair or tooth replacements, are arranged exclusively or preferably for their tissue integration, while at the same time cell species which interfere with this process, for example, blood platelets or fibroblasts which promote the formation of microthrombi or connective tissue capsules, are to be prevented from undergoing selective interaction with the implant.

It would furthermore be a desirable and attractive strategy to coat implants with those peptides defined according to the invention (or their non-peptide analogues) which exclusively or at least preferably stimulate the adhesion of those selected cell types which bear the corresponding complementary integrins, which as a result leads to the accelerated in vivo synthesis of the corresponding selected tissue.

With respect to the development of complete biohybrid organs (skin, blood vessels, urinary passages, bladder, oesophagus, pancreas, liver, spleen, kidney), it would be a decisive advance to be able to activate the desired various cell species in each case for a certain organ by coating different surface parts of an implant with various cell-selective peptides defined according to the invention in a targeted, spatially defined and coordinated manner for carrying out different cellular in vivo processes.

The present invention now describes the possibility of the biofunctionalization of biomaterials, in particular implants for all conceivable organs by coating thereof with synthesized cell- or tissue-selective RGD peptides defined according to the invention, which in vitro stimulate the adhesion mainly of those cell species which in each case should accomplish the tissue integration of the corresponding biomaterial and which at the same time in vitro do not stimulate the adhesion predominantly of those cell species which oppose this process. With the use of such coatings, an accelerated and enhanced integration of various biomaterials/implants can be achieved with improved long-term stability after their insertion into the body.

Moreover, with this concept of the coating of various material surface parts of an implant with different peptides defined according to the invention all possibilities exist for the development of "intelligent", biohybrid organs ("tissue engineering"), which can carry the biological information for the selective activation of various target tissue or target cells and thus can be integrated into the body by self-organization and by this means can enhance tissue integration or can even make it possible for the first time.

The invention thus relates to an implant which is suitable for different human and animal organs, consisting essentially of a carrier matrix and a peptide coating surrounding this matrix, which contains identical or different peptides for the targeted adhesion stimulation of human or animal body cells, which have sequences which recognize binding sites on the integrin receptors responsible for adhesion on human or animal cells, the carrier matrix having reactive groups capable of binding on its surface, which are capable of entering into a stable covalent bond with appropriate functional reactive groups of said peptide layer, the implant being distinguished in that said peptides are arranged in a locally differing manner on the surface of the implant such that on account of their correspondingly different structure-related, cell adhesion-stimulating activity they correspond specifically to the natural different complementary integrin pattern of the tissue cells adjoining them in the particular region into which cells the implant is to be inserted, by means of which a locally differentiated and selective, bioactive coating pattern of the implant surface is present.

The invention further relates to a process for the preparation of implants suitable for organs/tissue based on an inorganic carrier matrix which have a surface which is coated with the cell adhesion-stimulating peptides, said peptides being selective with respect to the complementary integrin pattern of the tissue cells immediately adjoining the implant, which is characterized in that, by methods known per se, (i) the integrin receptor structure of the target cells or of the target tissue in which the implant is to be introduced in vivo is determined in vitro, (ii) the peptides having the appropriate complementary structure are selected or synthesized and, (iii) said peptides are bonded to the relevant surface of the implant.

In particular, the invention relates to processes and implants/biomaterials having the following characteristics: said peptides, in particular RGD peptides, are attached to the implant surface by covalent bonding, if desired via branched, surface-enlarging molecules and/or molecular anchors; preferably RGD peptides are used which can stimulate alpha$_v$beta$_3$-/alpha$_v$beta$_5$-carrying cells, thus in particular, for example, the adhesion of osteoblasts, osteoclasts, endothelial cells, and at the same time are capable of not stimulating the adhesion of blood platelets or fibroblasts; carrier matrices employed are shaped or unshaped parts made of ceramic, polymer material or metal or a biohybrid organ or hollow organ.

At the molecular level, the peptides defined according to the invention are essentially designed from the following constituents:

- an amino acid sequence-bearing domain relevant for adhesion (e.g. the RGD sequence mentioned), which selectively recognizes and binds a selected cell species,
- a spacer in order to present the cell-recognizing and the recognition sequence-bearing domain to the cells in such a manner that cell binding is only possible from steric standpoints,
- a molecular anchor which effects the stable binding of the peptide derivative concerned to the biomaterial or implant surface,
- optionally cell adhesion can be increased by additional coupling of the peptides defined according to the invention to branched molecular structures (so-called dendrimers or Tentakels) which exert a surface-enlarging effect, before the binding to the biomaterial surface takes place.

The surface of the biomaterial or implant is to be understood according to the invention as not only the immediate surface of the carrier matrix, but also an additional coating which may be present of, for example, polymeric material, natural or artificial bone materials, proteins or protein derivatives.

Suitable carrier matrices are especially materials made of ceramic, metal, polymer materials (e.g. PMMA) or preferably resorbable bone replacement materials. Resorbable or biodegradable materials made, for example, from polylactides, in particular racemic D,L polylactide compounds or resorbable calcium phosphate or hydroxyapatite mixtures which can bring about the restoration of the original tissue state and such as are disclosed, for example, in WO 96/36562 or EP 0 543 765 are particularly suitable. Depending on the field of use, collagen or agar may also be suitable as a carrier matrix.

The term "biohybrid organ" is to be understood as meaning a customarily inorganic matrix which is loaded with or bonded to living cells in any manner (see above). According to the invention, this is also to be understood as meaning a corresponding arrangement which is free of cells and only contains the corresponding peptides of different types defined according to the invention on different implant surface parts, which, inserted into the defective tissue, are selectively able to activate the surrounding cells. The advantage of such acellular biohybrid organs is that "intelligent", biocompatible implants which can be produced in a cost-efficient and controllable manner carry the biological information for organ regeneration. The integration of such biohybrid organs into the body is then completed by means of self-organization by endogenous regeneration processes, by means of which immunological defence reactions, such as often occur, for example, due to implanted foreign cells or foreign proteins, can be avoided.

According to the invention, the implants as a rule are present in shaped bodies or prostheses, where the shaped body should be tailored to the particular tissue/bone defect. In the case of biohybrid organs, the prostheses can only consist of membranes or films coated with or without corresponding cells and the peptides defined according to the invention or else the arrangements such as are disclosed, for example, in EP 0 504 781.

Suitable peptides which can be employed according to the invention are all peptides and compounds thereof having non-peptide substituents which contain a domain or amino-acid sequence responsible for cell adhesion and which can bind to the implant surfaces via their peptide and non-peptide substituents. In particular, possible corresponding peptides are those having an RGD sequence.

The following list of preferred peptides and peptide compounds are only intended to have exemplary and no limiting character whatsoever, the following abbreviations being used:

Asp(D)=Aspartic acid
Gly(G)=Glycine
Arg(R)=Arginine
Tyr(Y)=Tyrosine
Ser(S)=Serine
Phe(F)=Phenylalanine
Lys(K)=Lysine
DPhe(f)=D-Phenylalanine
Pro(P)=Proline
Leu(L)=Leucine
Ile(I)=Isoleucine
Val(V)=Valine
Glu(E)=Glutamic acid
Thre(T)=Threonine
Ala(A)=Alanine (a) Examples of Suitable RGD-containing Peptides
RGD (Arg-Gly-Asp),
GRGD (Gly-Arg-Gly-Asp)(SEQ ID NO:1),
GRGDY (Gly-Arg-Gly-Asp-Tyr)(SEQ ID NO:2),
RGDS (Arg-Gly-Asp-Ser)(SEQ ID NO:3),
GRGDS (Gly-Arg-Gly-Asp-Ser)(SEQ ID NO:4),
RGDF (Arg-Gly-Asp-Phe)(SEQ ID NO:5),
GRGDF (Gly-Arg-Gly-Asp-Phe)(SEQ ID NO:6),
cyclo-RGDfK (Arg-Gly-Asp-DPhe-Lysine),
cyclo-RGDfKG (Arg-Gly-Asp-DPhe-Lys-Gly).

(b) Examples of Suitable Non-RGD-containing Peptides
LDV (Leu-Asp-Val),
LGTIPG (Leu-Gly-Thr-Ile-Pro-Gly)(SEQ ID NO:7),
REDV (Arg-Glu-Asp-Val)(SEQ ID NO:8),
IKVAV (Ile-Lys-Val-Ala-Val)(SEQ ID NO:9),
YIGSRG (Tyr-Ile-Gly-Ser-Arg-Gly)(SEQ ID NO:10),
LRE (Leu-Arg-Glu),
PDSGR (Pro-Asp-Ser-Gly-Arg)(SEQ ID NO:11),
DGEA (Asp-Gly-Glu-Ala)(SEQ ID NO:12),
RYVVLPR (Arg-Tyr-Val-Val-Leu-Pro-Arg)(SEQ ID NO:13).

The peptides defined according to the invention can be either linear or cyclic. The abovementioned peptides and peptide sequences can also occur within longer peptides having, depending on the peptide according to the invention selected, approximately a total of 4 to 20 amino acids. Likewise, amino acids which have the D or L configuration or which are C- and/or N-alkylated are also included according to the invention. Cyclic peptides are understood according to the invention as meaning those peptides which are closed to form a ring via an amide bond, preferably no free carboxyl or amino groups being present in the molecule. RGD peptides according to the invention are particularly preferred, in particular those from the abovementioned list and of these particularly the pentapeptide RGDfK, which in its cyclic form is disclosed in DE-A-1 95 38 741 and is specific for osteoblasts, and also the hexapeptide RGDfKG which is likewise present in its cyclic form and is specific for thrombocytes.

Corresponding linear and cyclic peptides defined according to the invention are described, for example, in the following Patent Applications: EP 0 632 053, EP 0 655 462, EP 0 578 083, EP 0 770 622, DE 1 95 38 741. In particular, those peptides are suitable which bind selectively to alpha$_v$beta$_3$-/alpha$_v$beta$_5$-integrin-expressing cell species (e.g. osteoblasts, osteoclasts, endothelial cells) without simultaneously binding to, for example, $\alpha_{IIb}\beta_3$-bearing cell species (e.g. blood platelets). The peptides and the corresponding derivatives can be easily synthesized by standard methods if they are not obtainable in another way.

In principle, the peptides defined according to the invention can be attached to the surface of the biomaterial by adsorption or covalent bonding. The adsorption method is less well suited when using different peptides on one and the same implant, since the locally selective differing coating of the surface according to the invention can only be effected in a poorly satisfactory manner using this technique.

The coupling of the peptides or their non-peptide analogues to carrier surfaces by covalent bonding mostly by means of so-called molecular anchors is adequately known per se and has been described, i.e., for example, in Singer et al. (1987, J. Cell. Biol. 104: 573); Brandley, Schnaar (1989, Develop. Biol. 135: 74); Massia, Hubbell (1990, Anal. Biochem. 187: 292); Hirano et al. (1991, J. Biomed. Mat. Res. 25: 1523); Lin et al. (1992, Biomaterials 13: 905); Nicol et al. (1992, J. Biomed. Mat. Res. 26: 393); Dee et al. (1995, Tissue Engin. 1: 135), without in this case, however, the coating of implants being gone into in general and in particular in any manner.

The present invention, then, relates to novel applications of coating methods known per se for the preparation of the implants according to the invention, such as, for example, the "Keyloc®" process (EP 0 712 621), which for the first time was employed according to the invention for the coupling of the peptides mentioned (or their non-peptide analogues) to surfaces which contain acryloyl or methacryloyl anchor components, or the "Silicoater®" process (DE-A 42 25 106), which was used here according to the invention for the coupling of the corresponding peptides by means of acryloyl or methacryloyl anchor components, as a rule via an acryloyl/methacryloyl silane derivative intermediate layer (e.g. 3-methacryl-oxypropyl trimethoxysilane) to the corresponding carrier matrices. A further possibility of bonding the peptides defined according to the invention to the surface of the carrier matrix or of the implant consists in the analogous use of a silanization process which is described in DE-A 43 21005, which originally explains the technical teaching for the coating of pearl luster pigments for water-based coating systems for metals and plastics in the automotive and plastics industry. A process for the coating of gold surfaces with thiol group-bearing peptides, which was originally described in another connection (Heuvel et al., 1993, Analytical Biochem. 215: 223) is furthermore suitable according to the invention.

The processes outlined have until now not been employed for the coating of implants for the purpose of bioactivation thereof.

The coupling of the corresponding peptides defined according to the invention to the implant surface takes place according to the invention via appropriate anchor molecules, i.e. the peptide is, as a rule, not directly attached itself to the implant surface. The insertion of such a molecule, defined in greater detail below, especially has the point of taking into account the steric requirements of the biological receptor on the target cells in connection with the binding of the corresponding peptide.

For this purpose, the implant surface must carry appropriate functional groups or reactive units which make possible binding of the corresponding functional group of the anchor molecule. The functional groups which are to be made available on the implant surface in turn depend on the composition of the actual carrier matrix, which differs according to requirement (metal, plastic, bone materials). In the case of metal implants, it is possible, for example, to generate a surface layer reactive for SH radicals of the anchor molecule by vapour deposition with gold. The silanization of metal surfaces according to known processes (see above) likewise leads to reactive surfaces which can enter into compounds with the suitable anchor molecules according to the invention, if appropriate using silane-containing adhesion promoters (see below). Implants made of natural bone or nature-like bone materials (e.g. calcium phosphate cements) can bond anchor molecules which contain a reactive phosphonate group (principle described in Chu, Orgel, 1997, Bioconjugates Chem. 8: 103). Anchor molecules according to the invention, which for their part themselves have a reactive acrylate radical, can in turn be coupled to implants made from acrylate-based plastic (e.g. PMMA) or from other materials having an appropriate plastic coating.

Anchor molecules in the sense of the invention are thus molecules based on modified or substituted alkyl chains or hydrocarbon chains which have at least two different functional groups, one functional group as a rule being a free carboxyl group (free NH$_2$ group) which generates an amide bond (—CO—NH—) with a free NH$_2$ group (free carboxyl group) of a side chain of a peptide defined according to the invention, in particular of an RGD peptide, and the other functional group, which is preferably localized at the other end of the C chain of the anchor molecule and brings about direct or indirect bonding to the implant surface, depending on the composition or requirement of the implant surface, preferably being a (meth)acrylate-containing radical or a mercapto group. In principle, it is also possible to use other functional groups which are able to react with the respective reactive groups directly on the implant surface or on a suitable intermediate layer to give a stable bond.

The anchor molecules of the invention, as already indicated above, at the same time have the function of spacers, i.e. besides their outlined linking options have an appropriate optionally specifically tailored length in order to make it possible that the domain responsible for cell adhesion stimulation has the right distance to the target cell so that cell bonding can be improved or even made possible from steric standpoints.

The biological function of the cell-recognizing and the corresponding amino acid sequence-bearing domain was confirmed by way of example by means of a synthetic peptide binding selectively to alpha$_v$beta$_3$-/alpha$_v$beta$_5$-integrin-expressing cell species (e.g. osteoblasts, osteoclasts, endothelial cells) (Haubner et al., 1996, J. Am. Chem. Soc., 118: 7461–7472).

The anchor molecules of the invention preferably have the following linear structures, the peptides defined according to the invention being bonded via the NH$_2$ group of one of their amino acid side chains, preferably a lysine side chain, to the free carboxyl end of the respective anchor molecule.

(i) Mercapto(amido)carboxylic acid derivatives:

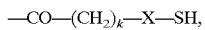

where X is a single bond or —CO—NH—(CH$_2$)$_l$—, k=2 to 12 and l=2 to 4;

(ii) Acrylamidocarboxylic acid derivatives:

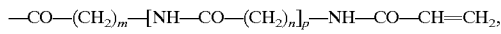

where m,n=2 to 8; p=0 to 2,
(iii) Acrylamido-amidotriethyleneglycolic acid derivatives:

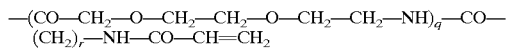

where q=1 to 3 and r=2 to 8.

In particular, the following types of specific anchor molecules are preferred:
(ia) —CO—CH$_2$—CH$_2$—SH (mercaptopropionic acid)
(ib) —CO—CH$_2$—CH$_2$—CO—NH—CH$_2$—CH$_2$—SH (mercaptoethyl-amidosuccinic acid)
(iia) —CO—(CH$_2$)$_5$—NH—CO—CH=CH$_2$ (acrylamidohexanoic acid)
(iib) —CO—(CH$_2$)$_5$—NH—CO—(CH$_2$)$_5$—NH—CO—CH=CH$_2$ (acrylamidohexanoic acid-amidohexanoic acid)
(iiia) —CO—CH$_2$—O—CH$_2$—CH$_2$—O—CH$_2$—CH$_2$—NH—CO—(CH$_2$)$_5$—NH—CO—CH=CH$_2$ (acrylamidohexanoic acid-amidotriethyleneglycolic acid)
(iiib) —(CO—CH$_2$—O—CH$_2$—CH$_2$—O—CH$_2$—CH$_2$—NH)$_2$—CO—(CH$_2$)$_5$—NH—CO—CH=CH$_2$ (acrylamidohexanoic acid-diamidotriethyleneglycolic acid)

Generally, according to the invention any anchor molecule structures are preferred which have at least six C atoms in the linear C chain. As a matter of fact, it was surprisingly found that this length of the anchor molecule is particularly favourable in order to achieve optimum results with respect to the accelerated and enhanced tissue integration of the implant. The indication of at least six C atoms in the linear chain relates according to the invention to the total length of the molecule between peptide and implant surface. Thus anchor molecules of the structures shown above having a shorter chain (e.g. type ia) are also suitable if still other unmentioned, chain-lengthening coupling components are inserted between peptide and implant surface.

The anchor molecules are bonded in amide form via the carboxyl function to the peptides defined according to the invention by standard methods, by means of which structures of the type peptide-NH—CO-anchor molecule result which, in turn, as presented, are attached to the implant, by means of which, in turn, constructs of the following type result: peptide-NH—CO-anchor molecule-implant (surface). Corresponding implant constructs are preferred which are composed of one of the defined peptides mentioned individually above, in particular RGD peptides, one of the generally and specifically defined anchor molecules individually mentioned above and an appropriately surface-reactive implant. The following implants are particularly preferred:
cyclo-RGDfK NH—CO—thiol derivatives (type: i)—implant,
cyclo-RGDfK NH—CO—acrylate derivatives (type: ii)—implant,
cyclo-RGDfK NH—CO—acrylate-glycol derivatives (type: iii)—implant,
cyclo-RGDfKG NH—CO—acrylate-glycol derivatives (type: iii)—implant,
in which the linear C chain of the entire anchor molecule has at least six C atoms.

Particularly preferred among these are:
cyclo-RGDfK NH—CO—thiol derivative (type: ib)—implant,
cyclo-RGDfK NH—CO—acrylate derivative (type: iia)—implant,
cyclo-RGDfK NH—CO—acrylate derivative (type: iib)—implant,
cyclo-RGDfK NH—CO—acrylate-glycol derivative (type: iiia)—implant,
cyclo-RGDfKG NH—CO—acrylate-glycol derivative (type: iiia)—implant,
cyclo-RGDfK NH—CO—acrylate-glycol derivative (type: iiib)—implant The preparation of these preferred structures is carried out by standard methods, or is described further below, or in the parallel application of the Applicant filed on the same day, which relates to the peptide anchor structures as such.

As already discussed further above, essentially three alternative routes are followed for the anchoring of the cell- or tissue-selective peptide derivatives described to biomaterial surfaces according to the invention, it being possible for the molecular recognition pattern of the domain carrying the respective RGD sequence to remain selectively unchanged for a certain cell type and the spacer, whereas the molecular anchor can be varied depending on the coupling variants mentioned, for example by:
  coupling of thiol peptide derivatives to gold-coated biomaterial surfaces (e.g. to type (i) anchor molecules);
  coupling of (meth)acryloyl peptide derivatives to acrylate- or methacrylate-coated biomaterial surfaces (e.g. to type (ii) or (iii) anchor molecules);
  coupling of (meth)acryloyl peptide derivatives to silane-coated biomaterial surfaces (e.g. to type (ii) or (iii) anchor molecules) using a (meth)acryloyl silane derivative as an adhesion promoter or intermediate layer (e.g. 3-methacryloxypropyl trimethyloxysilane).

The attainment of the critical minimum length of the anchor molecule for various peptide coupling variants to biomaterial surfaces is carried out by synthesis of the peptides defined according to the invention with the anchor molecules defined according to the invention of a chain length preferably having 6 to 24 C atoms and alternatively different hydrophobic/hydrophilic properties (e.g. by use of numerically different units of —CH$_2$— and/or amidohexanoic acid or ethylene glycol according to methods standard per se and subsequent testing of the biological activity by determination of the cell adhesion in vitro after coating of appropriate biomaterial surfaces).

In the manner described, depending on the material properties of the implant, a suitable coating process can be selected for the conditioning of the surfaces before the actual coupling with the peptide derivatives according to the invention. Moreover, depending on the tissue type or the cell type which is intended to accomplish the integration of the biomaterial/implant, coating with other peptides is possible which in turn activates the integrins of the corresponding target cell species in a targeted manner, such as, for example, alpha$_6$beta$_4$-integrin from epithelial cells (e.g. for the use of bone, jaw, skin or hair implants) or alpha$_{IIb}$beta$_3$-integrin from blood platelets. Alpha$_v$beta$_3$-specific RGD peptides have a selectivity for endothelial cells and osteoblasts, as a result of which, for example, they would be suitable for the coating of vascular prostheses or bone implants. By this means, it is possible to realize a suitable bioactivating surface coating for almost any desired organ for implants in the field of bone, vessel, tooth, skin and hair replacement.

Before appropriate implants or biohybrid organs according to the invention can be made available, the peptides suitable for the particular cell type must be tested and determined beforehand for biological activity in an in vitro test system in order to be able to carry out later a specific and selective coating of the implant which is to be inserted into the selected tissue.

The analysis of the integrin receptor structure of the target tissue or of the target cells into which the implant is to be inserted necessary for this purpose is carried out by means of customary, known, immunohistological processes, such as, for example, by means of immunofluorescence or the immunohistochemistry of tissue samples. The antibodies against various integrin receptors or their subunits necessary for this purpose are meanwhile known and available or can be accordingly produced by means of standard methods known per se, such as, for example, suitable immunizations.

The peptides defined according to the invention are covalently coupled in various concentrations to culture surfaces, for example of polystyrene coated with bovine serum albumin (BSA). The material of this test support does not play any essential part in the determination of the suitable peptides. Likewise, the coupling method used here is additionally of little importance. For practical reasons, the coupling in these determinations can also be carried out by means of incubation and adsorption of said peptides on the test support.

Subsequently, the adhesion of selected tissue cell cultures (e.g. osteoblasts) which are able to correspond in their adhesion properties to the cells which are to be activated in the natural tissue in vivo are investigated on the appropriately coated surfaces. The criterion for the selection of suitable cell cultures for the adhesion experiments consists in the comparable integration expression pattern for the target cells in vivo after implantation, for example their $alpha_v beta_3$-/$alpha_v beta_5$- or $alpha_{IIb} beta_3$-expression, which is verified by means of fluorescence-labelled antibodies against $alpha_v beta_3$-, $alpha_v beta_5$- or $alpha_{IIb} beta_3$-integrins, or against the $alpha_v$-, $alpha_{IIb}$, the $beta_3$- or against the $beta_5$-subunits of the integrin receptor by means of a fluorescence-activated cell sorter (FACS). In the case of other target cell species in vivo with different integrin receptor patterns, other antibodies accordingly have to be employed. These are meanwhile known and available or can be produced according to known standard methods, e.g. by means of a suitable immunization.

The various selected cell species are inoculated and incubated on BSA-pretreated polystyrene culture surfaces coated with the peptides under consideration. Non-adherent cells are then washed off.

The binding behaviour of the different, selected cell species on the test surfaces coated with different peptides defined according to the invention corresponds in the positive case, that is to say if an adequate specificity is present, in each case to a titration curve having a maximum adsorption rate of approximately 60 to 100% of the inoculated cells and to a half-maximal cell binding at an RGD peptide concentration in the coating solution of approximately 5 nM to 5 $\mu$M.

In a similar manner, as described for the coupling of suitable peptides to BSA-precoated polystyrene surfaces, anchoring strategies to modified or conditioned biomaterial surfaces are possible using various adhesion promoter intermediate layers.

As a summary, the following can be said:

The implants of the prior art have the following disadvantages:
  incomplete, slow implant integration into the tissue,
  restricted acceptance in the tissue,
  inadequate functional stability of the implant/tissue border layer
  lack of stimulating action of the implant on tissue neogenesis
  non-physiological properties of the implant surface.

As consequences of this further problems result:
  aseptic implant loosenings (e.g. fibrous capsule formation)
  local formation of microthrombi,
  infections,
  inflammations,
  tissue resorptions,
  revisions.

These problems can be largely eliminated by the process made available according to the invention or the implants produced thereby. The subjects according to the invention are distinguished by:
  made-to-measure design of adhesion peptides, which are complementary to the integrin expression pattern of the target tissue/target cells;
  selective stimulation of the cell adhesion of the target cells which are to accomplish the tissue neogenesis without simultaneously causing the adhesion of the cells which prevent the process;
  coatings of higher stability by means of novel peptide anchor molecules;
  acceleration and enhancement of the implant integration process into the tissue.

It was possible to show that the critical steric absolute minimum distance between cell recognition sequence on the peptide and uncoated material surface is between 2.0 and 3.5 nm, preferably between 2.5 and 3.5 nm. Maximum coating rates (80–100%) can be achieved with a minimum distance of 3.0 to 5.0 nm.

BRIEF DESCRIPTION OF THE FIGURES

x axis: Fluorescence intensity (counts)
  y axis: Cell count
  M21: $alpha_v beta_3$- and $alpha_v beta_5$-positive controls
  M21: $alpha_v beta_3$- and $alpha_v beta_5$-negative controls
  HOB: culture of primary human osteoblasts
  ROB: culture of primary rat osteoblasts

x axis: RGD peptide concentration in the coating solution ($\mu$M),
  y axis: Degree of cell coating (%);
  Upper curve: cyclo-RGDfK NH—CO—$CH_2$—$CH_2$—S— (sulpho-SMPB) ("Thiolpeptide 1-SMPB derivative"), SMPB=succinimidyl 4-(p-maleimidophenyl)butyrate;
  Middle upper curve: cyclo-RGDfK NH—CO—$CH_2$—$CH_2$—CO—NH—$CH_2$—$CH_2$—S— (sulpho-SMPB) ("thiolpeptide 2-SMPB derivative")
  Middle lower curve: cyclo-RGDvE CO—NH—$CH_2$—$CH_2$—$CH_2$—$CH_2$—CO—NH—$CH_2$—$CH_2$—S— (sulpho SMPB) ("thiolpeptide 3-SMPB derivative")
  Lower curve: thiolpeptide control: cyclo-R$\beta$ADfK-NH—CO—$CH_2$—$CH_2$—S— (sulpho-SMPB)

Figure 2:
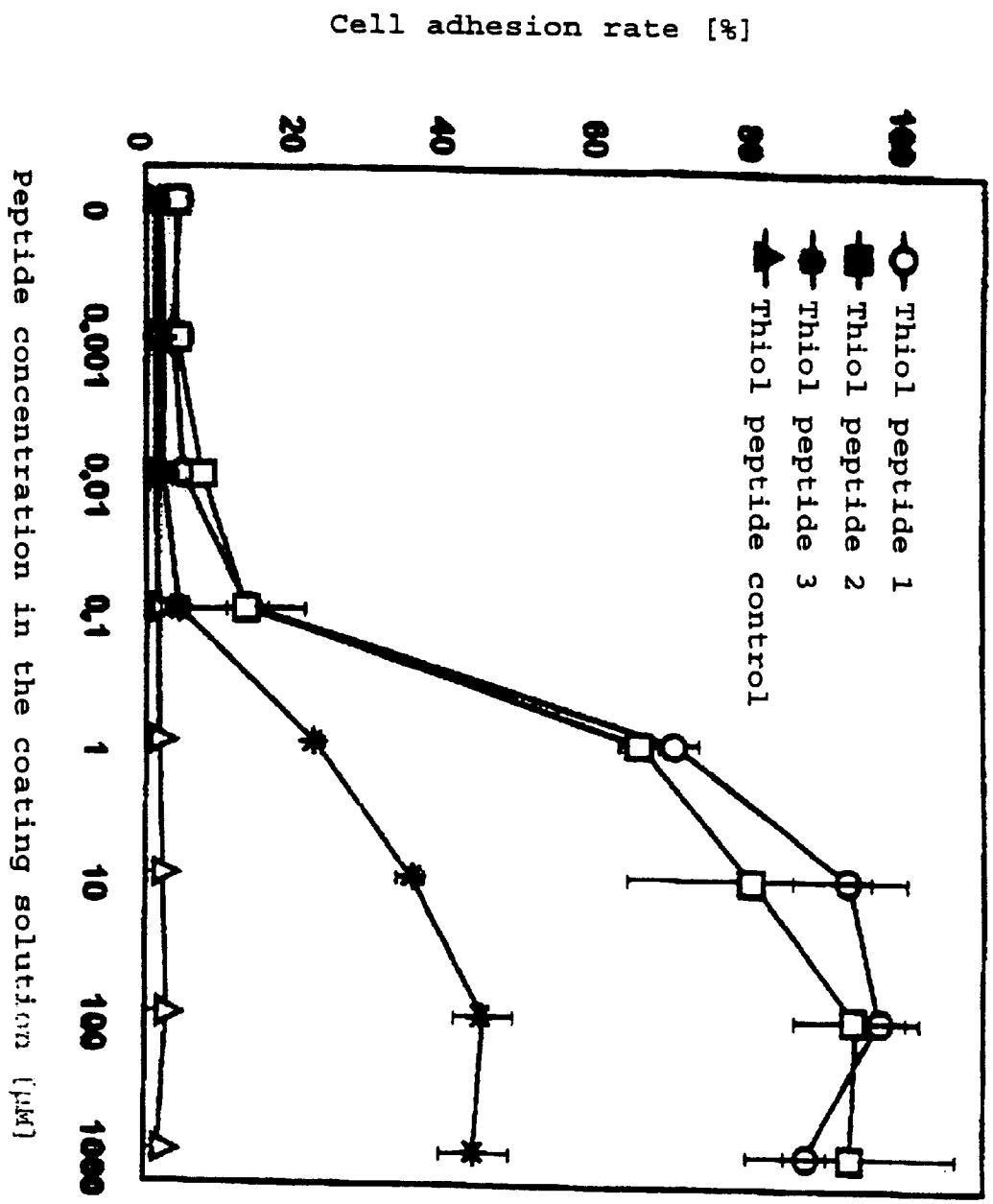
FIG. 2: Adhesion of MC3T3 H1 osteoblasts to polystyrene test surfaces coated with various RGD peptides via BSA.
Figure 3:
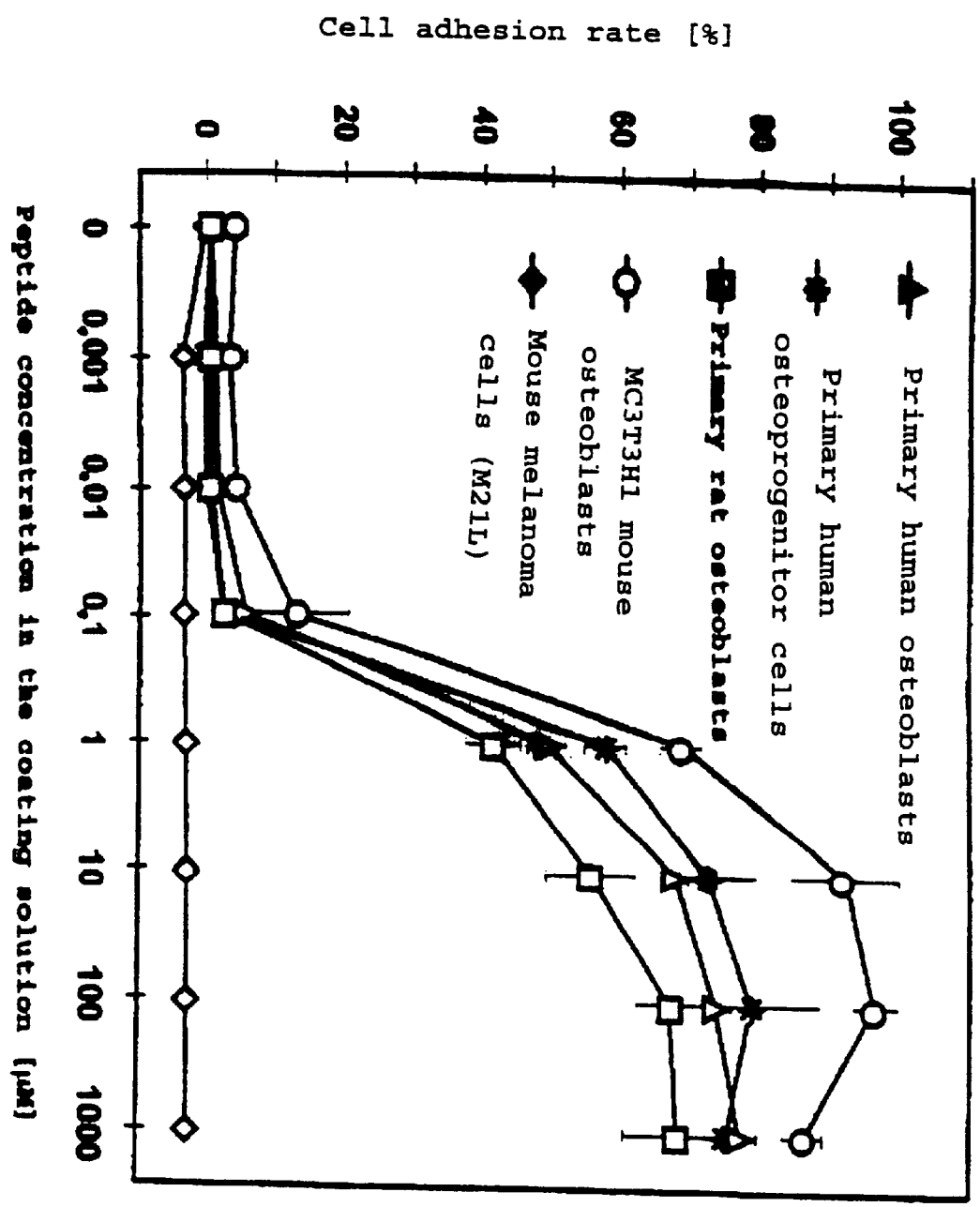

FIG. 3: Adhesion of osteoblasts to test surfaces coated with thiolpeptide 1-SMPB derivative (see under FIG. 2):
  x axis: Peptide concentration in the coating solution ($\mu$M),
  y axis: Degree of cell coating (%),
  Upper curve: MC3T3 H1 mouse osteoblasts;
  Middle upper curve: Primary human osteoprogenitor cells
  Middle curve: Primary human osteoblasts
  Middle lower curve: alpha$_v$beta$_3$-negative control cells M21L
  Lower curve: Primary rat osteoblasts FIG. 4: Adhesion of osteoblasts to test surfaces coated with thiolpeptide 1-SMPP derivative (10 $\mu$M in the coating solution) (see FIG. 2)
  x axis: Concentration of dissolved cyclo-RGDfK (without molecular anchor) in the adhesion medium ($\mu$M),
  y axis: Degree of cell coating (%);
  Upper curve: MC3T3 H1 mouse osteoblasts;
  Middle curve: Primary human osteoblasts
  Lower curve: Primary rat osteoblasts.

Figure 5:
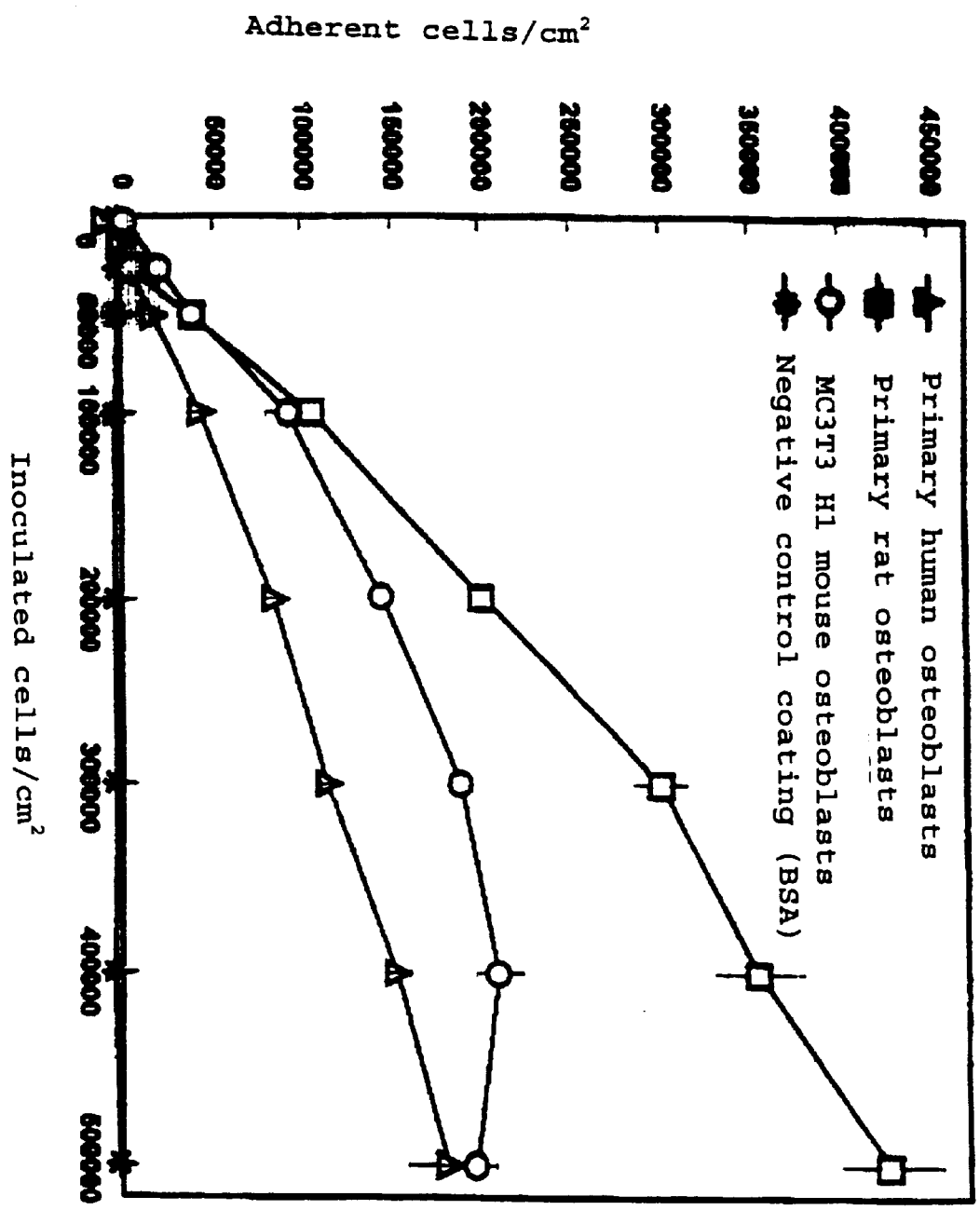

FIG. 5: Adhesion of osteoblasts to test surfaces coated with thiolpeptide 1-SMPB derivative (10 $\mu$M in the coating solution) (see FIG. 2),
  x axis: Number of inoculated cells/cm$^2$
  y axis: Number of adhered cells/cm$^2$
  Upper curve: Primary rat osteoblasts
  Middle upper curve: MC3T3 H1 mouse osteoblasts;
  Middle lower curve: Primary human osteoblasts
  Lower curve: BSA negative coating.

Figure 6:
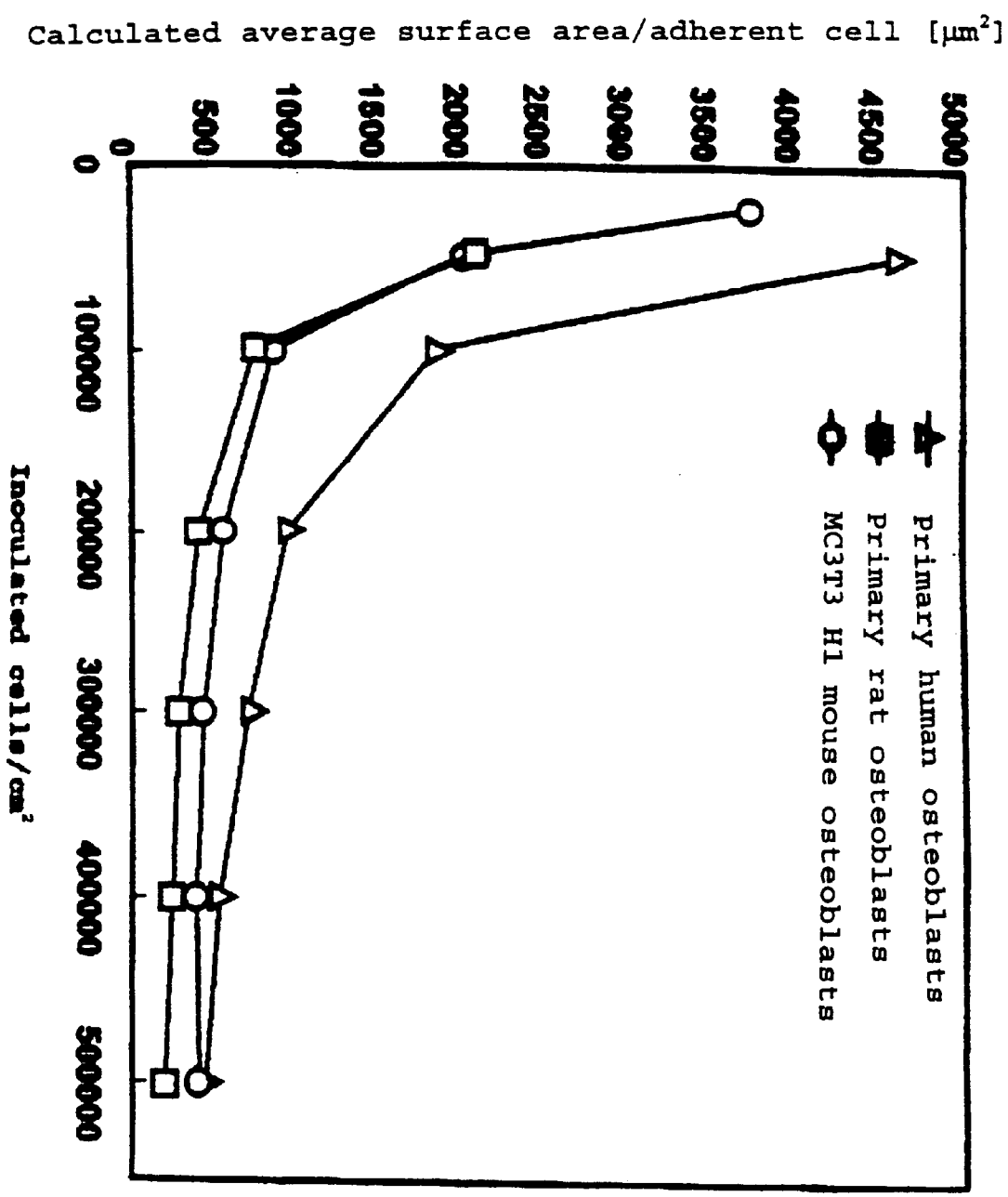

FIG. 6: Adhesion of osteoblasts to test surfaces coated with thiolpeptide 1-SMPB derivative (10 $\mu$M in the coating solution) (see under FIG. 2),
  x axis: Number of inoculated cells/cm$^2$
  y axis: Calculated surface area requirement/cells ($\mu$m$^2$)
  Upper curve: Primary human osteoblasts
  Middle curve: MC3T3 H1 mouse osteoblasts;
  Lower curve: Primary rat osteoblasts FIG. 7: Adhesion of osteoblasts to test surfaces coated with thiolpeptide 1-SMPB derivative (10 $\mu$M in the coating solution) (see under FIG. 2),
  x axis: Time (min)
  y axis: Degree of cell coating (%)
  Upper curve: MC3T3 H1 mouse osteoblasts;
  Middle curve: Primary human osteoblasts
  Lower curve: Primary rat osteoblasts FIG. 8: Adhesion of MC3T3 H1 osteoblasts to bone cement-PMMA surfaces coated with various RGD peptides:
  x axis: RGD peptide concentration in the coating solution ($\mu$M),
  y axis: Degree of cell coating (%)
  Upper curve: cyclo-RGDfK NH—CO-acrylate derivative (type: iiia, acrylate peptide 3),
  Middle upper curve: cyclo-RGDfK NH—CO-acrylate derivative (type: iib, acrylate peptide 2),
  Middle lower curve: cyclo-RGDfK NH—CO-acrylate derivative (type: iiib, acrylate peptide 4),
  Lower curve: cyclo-RGDfK NH—CO-acrylate derivative (type: iia, acrylate peptide 1), FIG. 9: Adhesion of MC3T3 H1 osteoblasts to porous PMMA/PHEMA surfaces coated with various RGD peptides:
  x axis: RGD peptide concentration in the coating solution ($\mu$M),
  y axis: Degree of cell coating (%)
  Upper curve: cyclo-RGDfK NH—CO-acrylate derivative (type: iiia, acrylate peptide 3),
  Middle curve: cyclo-RGDfK NH—CO-acrylate derivative (type: iiib, acrylate peptide 4),
  Lower curve: cyclo-RGDfK NH—CO-acrylate derivative (type: iib, acrylate peptide 2), FIG. 10: Adhesion of MC3T3 H1 osteoblasts to porous PMMA/Plex Y7H surfaces coated with various RGD peptides:
  x axis: RGD peptide concentration in the coating solution ($\mu$M),
  y axis: Degree of cell coating (%)
  Upper curve: cyclo-RGDfK NH—CO-acrylate derivative (type: iiia, acrylate peptide 3),
  Middle curve: cyclo-RGDfK NH—CO-acrylate derivative (type: iiib, acrylate peptide 4),
  Lower curve: cyclo-RGDfK NH—CO-acrylate derivative (type: iib, acrylate peptide 2), FIG. 11: Maximal adhesion of MC3T3 H1 osteoblasts to bone cement-PMMA or polystyrene-BSA-SMPB surfaces coated with various RGD peptides of varying molecular lengths:
  x axis: RGD peptide molecule lengths (nm)
  y axis: Maximal degree of coating (%)

Figure 12:
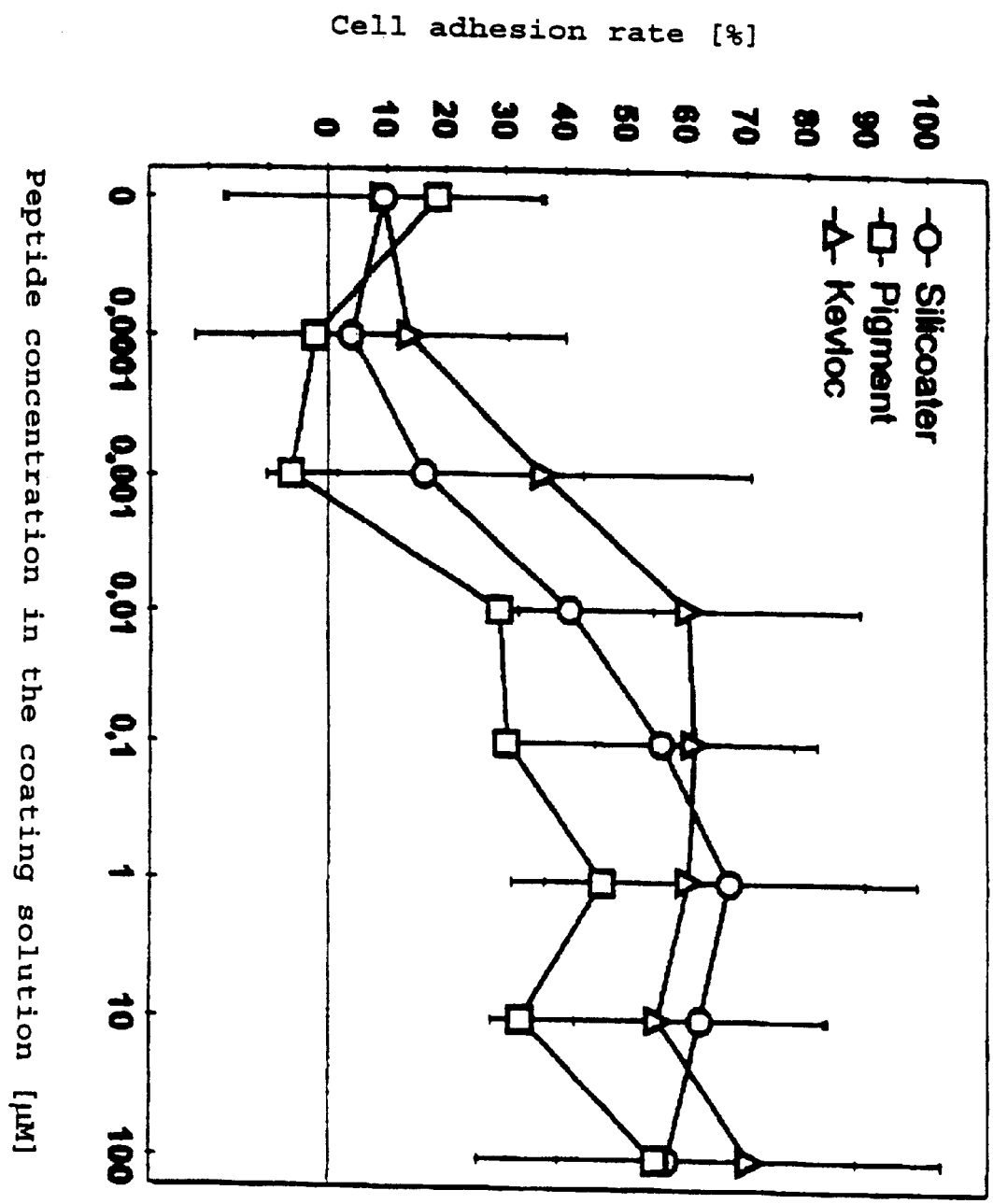

FIG. 12: Adhesion of MC3T3 H1 osteoblasts to V4A stainless steel surfaces coated with RGD peptide cyclo-RGDfK NH—CO-acrylate derivative (type iiia, acrylate peptide 3). The stainless steel surfaces, for their part, have previously been coated using various processes.
  x axis: RGD peptide concentration in the coating solution ($\mu$M)
  y axis: Degree of cell coating (%);
  Upper curve: Kevloc® coating;
  Middle curve: Silicoater® coating;
  Lower curve: Pigment coating.

Figure 13:
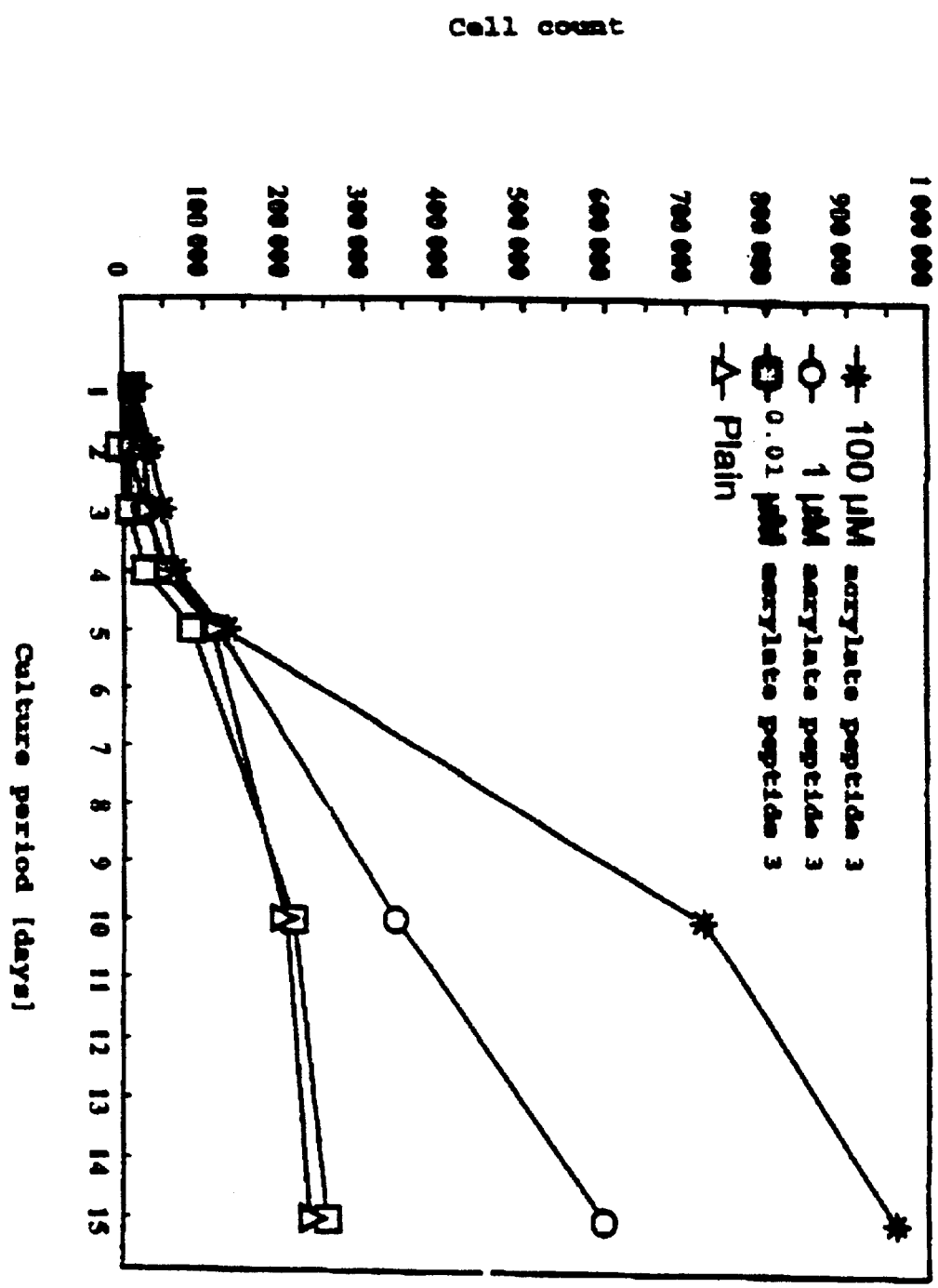

FIG. 13: Proliferation of MC3T3 H1 osteoblasts on bone cement-PMMA surfaces coated with RGD peptide cyclo-RGDfK NH—CO-acrylate derivative (type iiia, acrylate peptide 3).
  x axis: Culturing period (days),
  y axis: Cell count;
  Upper curve: 100 $\mu$M peptide in the coating solution;
  Middle upper curve: 1 $\mu$M peptide in the coating solution;
  Middle lower curve: 0.1 $\mu$M peptide in the coating solution;
  Lower curve: Uncoated control.

Figure 14:
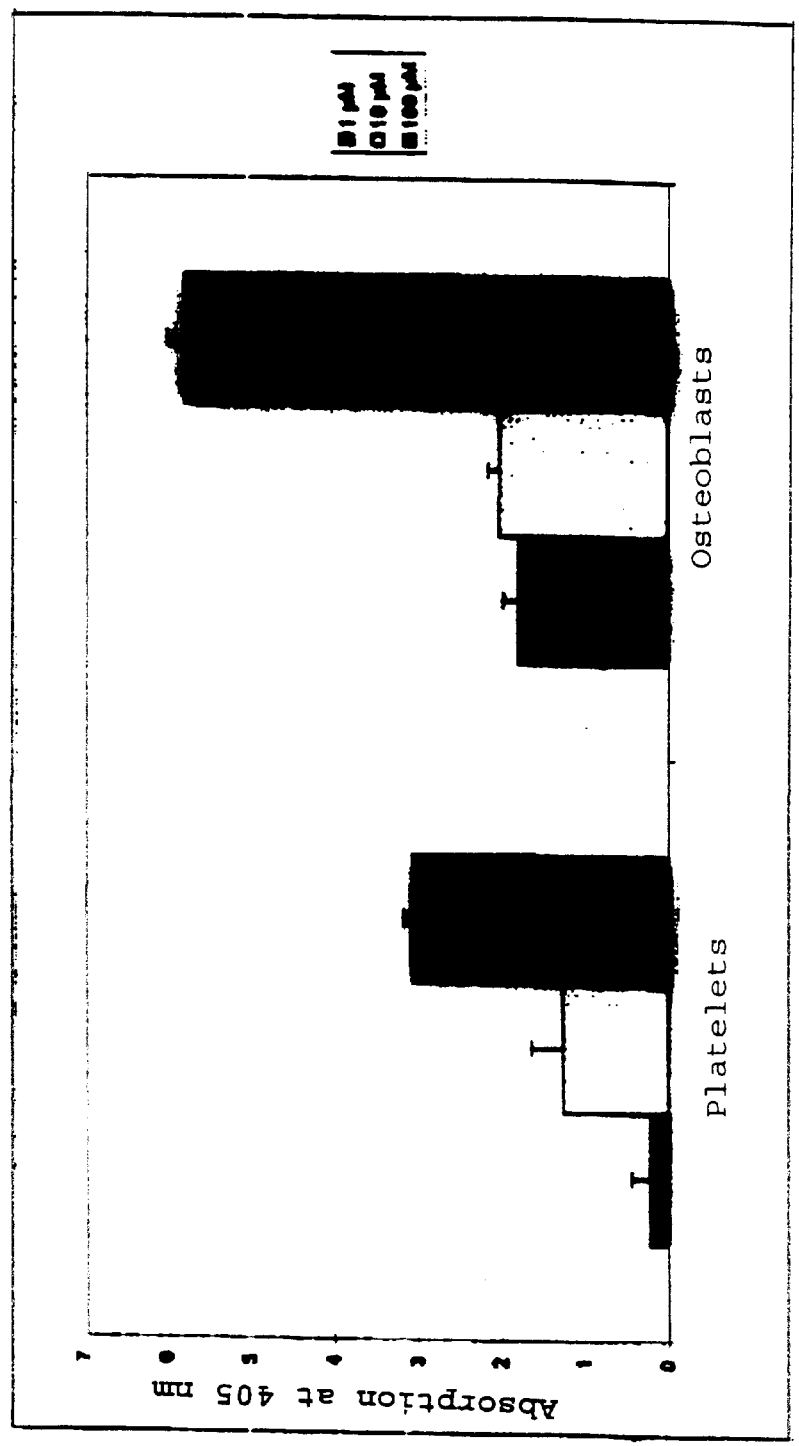

FIG. 14: Adhesion of MC3T3 H1 osteoblasts and platelets to bone cement-PMMA surfaces coated with RGD peptide cyclo-RGDfK NH—CO-acrylate derivative (type: iiia, acrylate peptide 3).
  x axis: Osteoblasts alone and platelets alone inoculated onto surfaces having various peptide concentrations in the coating solution of 100 $\mu$M, 10 $\mu$M and 1 $\mu$M.
  y axis: Cell count (absorption at 405 nm).

Figure 15:
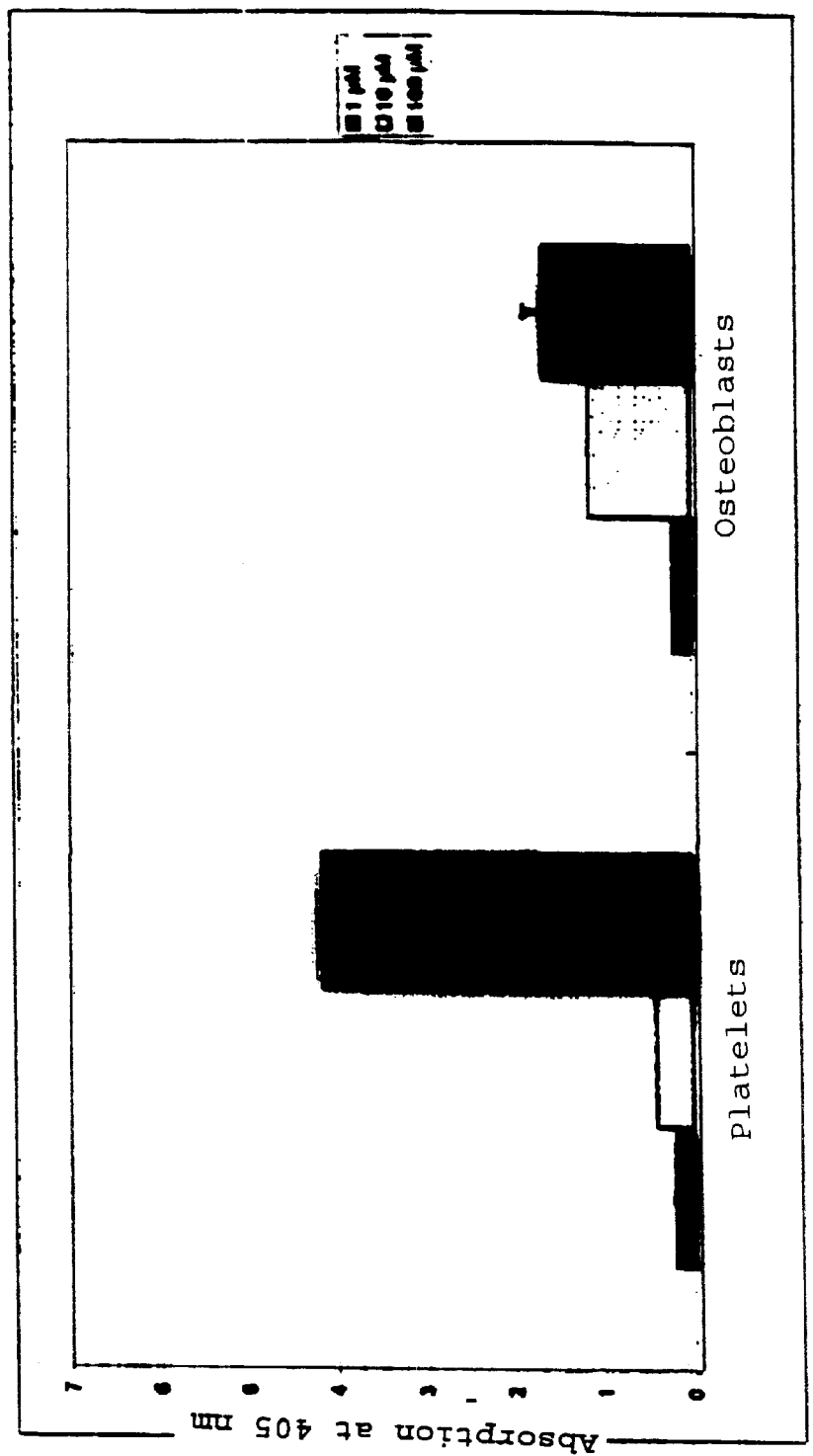

FIG. 15: Adhesion of MC3T3 H1 osteoblasts and platelets to bone cement-PMMA surfaces coated with RGD peptide cyclo-RGDfKG NH—CO-acrylate derivative (type: iiia, acrylate peptide 5).
  x axis: Osteoblasts alone and platelets alone inoculated onto surfaces having various peptide concentrations in the coating solution of 100 $\mu$M, 10 $\mu$M and 1 $\mu$M.
  y axis: Cell count (absorption at 405 nm).

Figure 16:
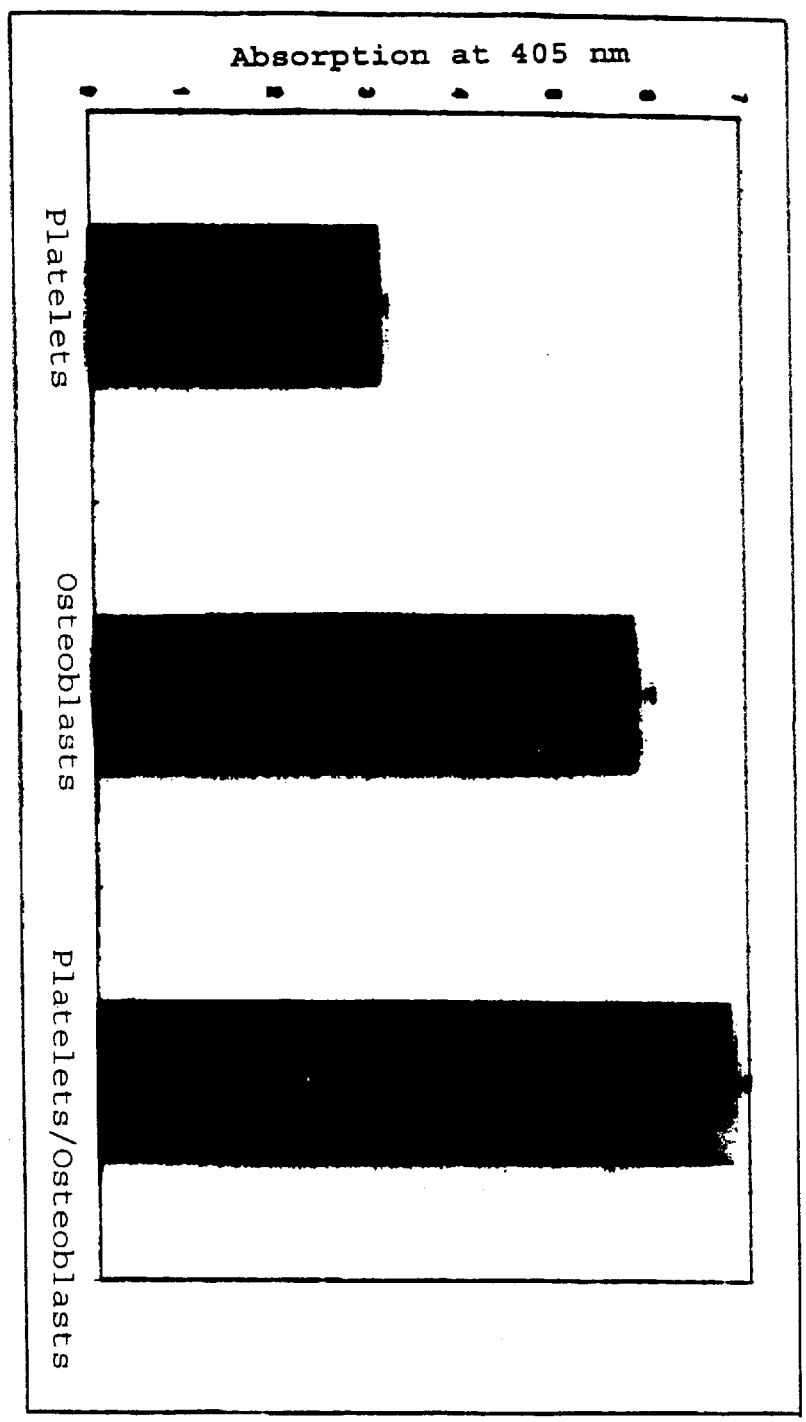

FIG. 16: Adhesion of MC3T3 H1 osteoblasts, platelets and an osteoblasts/platelets mixture to bone cement-PMMA surfaces coated with RGD peptide cyclo-RGDfK NH—CO-acrylate derivative (type: iiia, acrylate peptide 3).

x axis: Osteoblasts alone, platelets alone and osteoblasts/platelets mixture inoculated onto surfaces with the peptide concentration in the coating solution of 100 µM.

y axis: Cell count (absorption at 405 nm)

Figure 17:
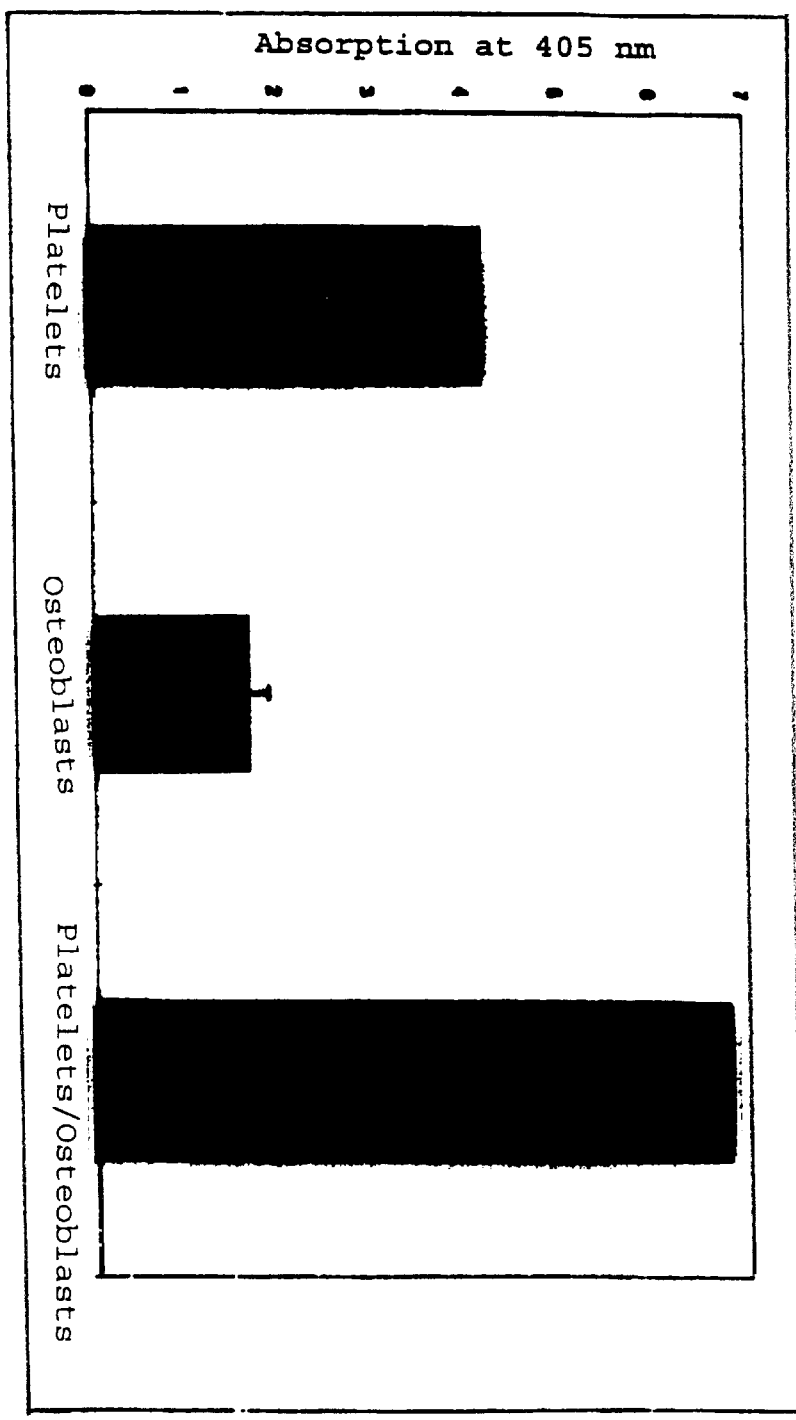

FIG. 17: Adhesion of MC3T3 H1 osteoblasts, platelets and an osteoblasts/platelets mixture to bone cement-PMMA surfaces coated with RGD peptide cyclo-RGDfKG NH—CO-acrylate derivative (type: iiia, acrylate peptide 5).

x axis: Osteoblasts alone, platelets alone and osteoblasts/platelets mixture inoculated onto surfaces with the peptide concentration in the coating solution of 100 µM.

y axis: Cell count (absorption at 405 nm)

The following examples illustrate the invention further without restricting it.

EXAMPLE 1

(a) The synthesis of the cyclo-RGD peptide (Arg-Gly-Asp-DPhe-Lys) with the anchor mercaptopropionic acid (→cyclo-RGDfK NH—CO-thiol derivative type: ia) was carried out according to the process from DE 1 95 38 741. The synthesis of the corresponding cyclo-RβADfk derivative which is biologically inactive and of the cyclo-RGDfK derivative without an anchor molecule was carried out analogously.

(b) cyclo(R(Pbf)GD(tBu)fK(Z)) (Pbf=pentamethylbenzofuransulphonyl; tBu=tert-butyl) was obtained by solid-phase peptide synthesis (Merrifield, Angew. Chem. 1985, 97: 801) and subsequent cyclization (e.g. according to Zimmer et al., 1993, Leibigs Ann. Chem: 497). After selective removal of the Z-protective group by standard methodology, the lysine side chain can be extended by reaction of 0.1 mmol of cyclo(R(Pbf)GD(tBu)fK) with 0.2 mmol of succinic anhydride (sa) in 5 ml of dimethylformamide to give cyclo(R(Pbf)GD(tBu)fp[sa-K].

(c) The synthesis of the cyclo-RGD peptide (Arg-Gly-Asp-DPhe-Lys) with the anchor mercaptoethyl-amidosuccinic acid (→cyclo-RGDfK NH—CO-thiol derivative type: ib=cyclo(RGDf[thiol-sa-K]) was carried out as follows: 10 mmol of cysteamine hydrochloride and an equimolar amount (eq.) of triphenylmethanol were dissolved in glacial acetic acid at 60° C. and treated with 1.1 eq. of BF₃ etherate with stirring. After stirring for 50 minutes, the mixture was neutralized with saturated NaHCO₃ solution and extracted with ethyl acetate. The oil remaining from the extract was dissolved in tert-butanol for conversion into the hydrochloride, brought to pH=2 with dilute hydrochloric acid and freeze-dried. Yield 99%. The structural unit thus obtained is coupled using EDClxHCl according to standard methods to cyclo(R(Pbf)GD(tBu)f[sa-K]) and the lateral protective groups are removed.

(d) The synthesis of the cyclo-RGD peptide (Arg-Gly-Asp-DPhe-Lys) with the anchor acrylamidohexanoic acid (→cyclo-RGDfK NH—CO-acrylic derivative type: iia=cyclo(RGDf[acrylic-ahx-K]) was carried out as follows:

The acrylic anchor system was synthesized separately and coupled to the peptide side chain as an active ester. To do this, 10 mmol of 6-aminohexanoic acid and 1.8 eq. of calcium hydroxide were suspended in water and 1.2 eq. of acryloyl chloride were added at 0° C. Insoluble calcium hydroxide was filtered off and the filtrate was acidified to pH 2 using concentrated hydrochloric acid. The precipitated product was recrystallized from ethyl acetate. Yield: 65%. 10 mmol of the crystalline 6-acrylamidohexanoic acid were suspended in 50 ml of dichloromethane, treated with 1 eq. of N-hydroxysuccinimide and 1.2 eq. of EDClxHCl were added at 0° C. After stirring for one hour, the reaction was stopped by addition of 10 µl of glacial acetic acid. It was extracted several times with cold, saturated sodium carbonate solution and with water and the extract was then dried over sodium sulphate. Yield: 52%. The active ester now present was coupled to cyclo(R(Pbf)GD(tBu)fK) in DMF and the side-chain protective groups were removed by standard procedures.

(e) The synthesis of the cyclo-RGD peptide in (Arg-Gly-Asp-DPhe-Lys) with the anchor acrylamidohexanoic acid-amidohexanoic acid (→cyclo-RGDfK NH—CO-acrylic derivative type: iib=cyclo(RGDf[acrylic-ahx-ahx-K]) was carried out as follows:

For the synthesis of the acrylic anchor system, 10 mmol of aminohexanoic acid are dissolved in aqueous sodium phosphate buffer (pH 8) and cooled to 0° C. 2 mmol of acrylamidohexanoic acid active ester (see (d)) were dissolved in ethanol/CHCl₃ and slowly added. The pH was kept constant at 8 using dilute NaOH. After distilling off the organic solvent, the aqueous phase was acidified to pH 2.6 using concentrated hydrochloric acid and the precipitated solid was filtered off, washed with water and dried over phosphorous pentoxide. Yield: 70%. The acrylic anchor system now present is coupled to the peptide side chain by methods known per se using EDClxHCl and the protective groups are removed.

(f) The synthesis of the cyclo-RGD peptide (Ary-Gly-Asp-DPhe-Lys) with the anchor acrylamidohexanoic acid-amidotriethyleneglycolic acid (→cyclo-RGDfK NH—CO-acrylic derivative type: iiia=cyclo(RGDf[acrylic-ahx-tEG-K]) was carried out as follows:

The acrylic anchor system was prepared by solid-phase peptide synthesis (see above). Acrylamidohexanoic acid (see above) was coupled as the last component. Yield: 97%. The acrylic anchor system now present is coupled to the peptide side chain by methods known per se using EDClxHCl and the protective groups are removed.

(g) The synthesis of the cyclo-RGD peptide (Arg-Gly-Asp-DPhe-Lys) with the anchor acrylamidohexanoic acid-amidotriethyleneglycolic acid-amidotriethyleneglycolic acid (→cyclo-RGDfK NH—CO-acrylic derivative type: iiib=cyclo(RGDf[acrylic-ahx-tEG-tEGK]) was carried out analogously to (f). Yield: 85%.

(i) The synthesis of the cyclo-RGD peptide (Arg-Gly-Asp-DPhe-Lys-Gly) with the anchor acrylamidohexanoic acid-amidotriethyleneglycolic acid (→cyclo-RGDfK NH—CO-acrylic derivative type: iiia=cyclo (RGDf[acrylic-ahx-tEG-KG]) was carried out analogously to (f). Yield: 81%.

EXAMPLE 2

The covalent coupling of the peptides according to the invention with sulphosuccinimidyl 4-(p-maleimidophenyl) butyrate (sulpho-SMPB) to culture surfaces of polystyrene precoated with bovine serum albumin (BSA) was accomplished following the established processes of Singer et al., 1987, J. Cell. Biol. 104: 573, or of Ruoslahti et al. (1982, Methods. Enzymol., 82: 803–831).

To do this, 48-well plates (Costar, "non-tissue culture treated", Art. No. 3547) were each coated with 250 µl of PBS (phosphate-buffered saline), pH=8.3, 2% BSA, per well and incubated overnight at room temperature in order to generate a BSA layer on the polystyrene. The plates were then washed with 250 µl of PBS, pH=8.3, per well and incubated at room temperature for 1 hour with 250 µl each of a solution containing 100 µg/ml of SMPB in PBS, pH 8.3. Washing of the wells was then carried out three times using 250 µl of PBS, pH 8.3, each time. For the preparation of the coating solutions, the appropriate thiol-RGD peptide was prepared in the following final concentrations in PBS, pH 8.3: 1 nM, 10 nM, 100 nM, 1 µM, 10 µM, 100 µM and 1 mM. After addition of 250 µl each of coating solution/well, the plates were incubated at room temperature overnight and then washed three times with PBS, pH 8.3. By addition of 250 µl each of a 5% strength BSA solution in PBS, pH 7.4, subsequent incubation for 2 hours at room temperature and washing with PBS, pH 7.4, non-specific cell-binding sites were blocked. Polystyrene surfaces, which from the coating were treated with a 5% strength BSA solution identically to the positive samples, functioned as negative coating controls. The adhesion of four cell cultures which were obtained from three different species was then investigated on the abovementioned surfaces coated with RGD peptide:

primary human osteoblasts from the head of the femur spongiosa of adult patients (Siggelkow et al., 1997, Bone 20: P231);

primary human osteoprogenitor cells from the bone marrow of adult patients (Vilamitjana-Amedee et al., 1993, In vitro Cell Dev. Biol. 29: 699);

primary osteoblasts from the calvaria of neonatal rats, whose preparation and culturing was carried out following the method of Yagiela and Woodbury (1977, The Anatomical Record, 188: 287–305);

osteoblast cell line MC3T3 H1, obtained from the calvaria of neonatal mice (Heermeier et al., 1995, Cells and Materials, 5: 309–321), and human melanoma cell line M21L as $alpha_v beta_3$/$alpha_v \beta 5$-integrin negative control.

Figure 1:
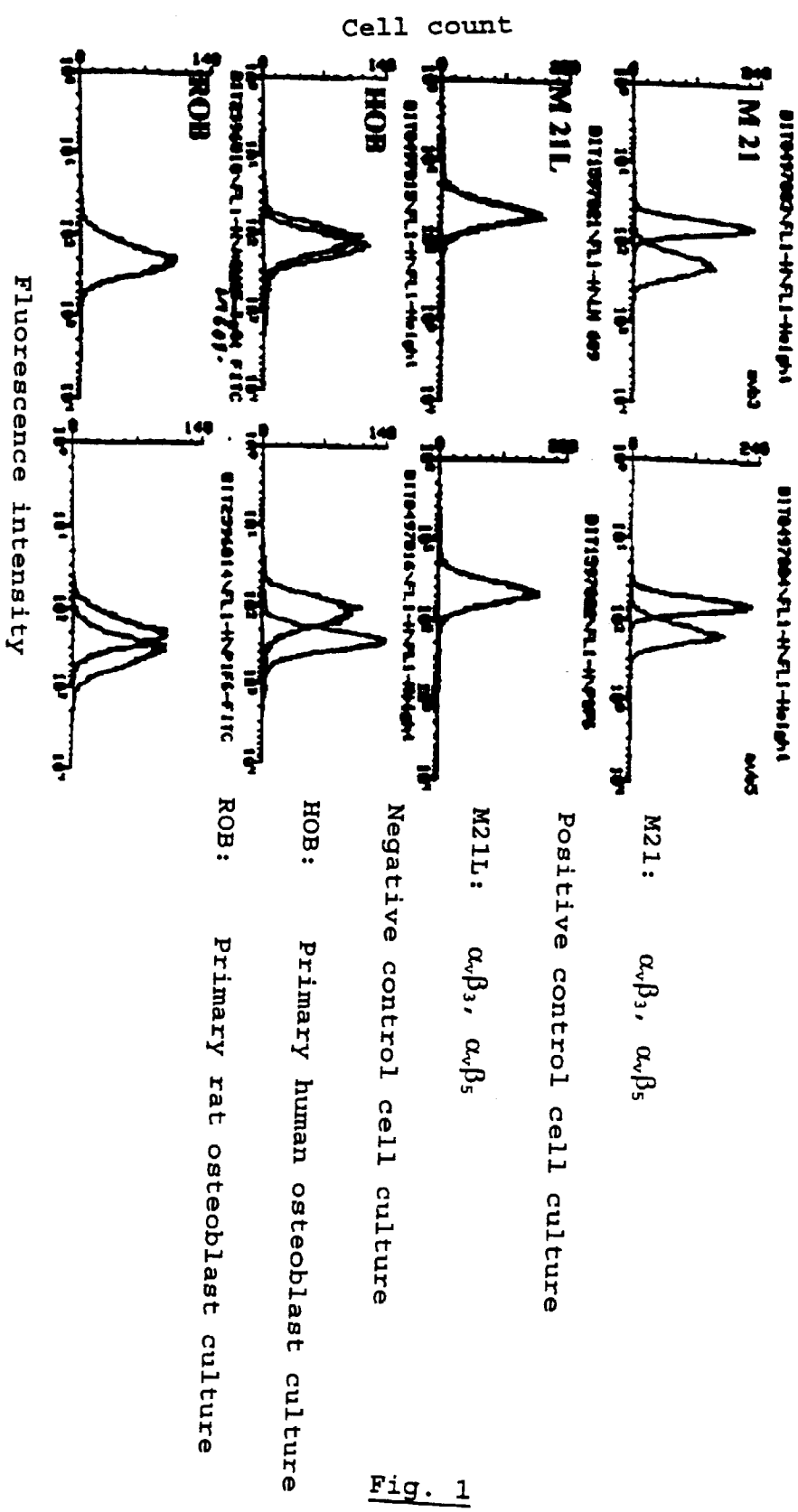
FIG. 1: Analysis of the integrin composition of primary human osteoblasts by FACS (fluorescence-activated cell sorter) by means of fluorescence-conjugated antibodies against $alpha_v beta_3$- and $alpha_v beta_5$-integrins.

Before these cell species were employed for the adhesion experiments, their integrin expression was verified by means of fluorescence-labelled antibody against the $alpha_v beta_3$- or $alpha_v beta_5$-receptors and against the integrin subunits $alpha_v$, $beta_3$ and $beta_5$ with the aid of a Becton-Dickenson fluorescence-activated cell sorter (FACS). A strong expression of said integrins was seen in this case (FIG. 1).

The cell species described were inoculated with an inoculation density of 48,000 cells/$cm^2$ into, as described above, Costar-48 well plates coated with RGD peptide, and then incubated for 1 hour at 37° C., 95% atmospheric humidity and 5% $CO_2$. Cells unadhered during the experiment were then washed off twice with PBS, pH 7.4.

The quantification of the adhered cells was carried out indirectly via the activity determination of the cellular enzyme N-acetylhexosaminidase using an appropriate standard curve according to the method of Landegren (1984, J. Immunol. Methods, 67: 379–388).

The coating of BSA-pretreated polystyrene cell culture surfaces with the $alpha_v beta_3$- or $alpha_v beta_5$-selective thiolpeptides 1-, 2-(sulpho-SMPB) derivatives leads to a strong and dose-dependent stimulation of the adhesion of cultured mouse MC3T3 H1 osteoblasts (see FIG. 2). In contrast to this, the biologically inactive thiolpeptide control has no significant effect, as a result of which the high selectivity and the high specificity of the integrin-RGD peptide interaction is shown. The less $alpha_v beta_3$-/$alpha_v beta_5$-selective thiolpeptide 3-(sulfo-SMPB) (cyclo-RGDvE-aminocysteinamidohexanoic acid: Delforge et al., 1996, Anal. Biochem. 242, 180) also shows a markedly weaker effect than the corresponding thiolpeptide 1 and 2 derivatives.

The binding behaviour of the different cell species to BSA-pretreated polystyrene surfaces coated with thiolpeptide 1-(sulpho-SMPB) derivative or thiolpeptide 2-(sulpho-SMPB) derivative corresponds to a titration curve having a maximum adsorption rate of about 70% (primary rat osteoblasts), about 80% (primary human osteoblasts and primary human osteoprogenitor cells) and about 90–100% (MC3T3 H1 mouse osteoblasts) of the inoculated cells, and a half-maximal cell binding with an RGD peptide concentration in the coating solution of 50–1000 nM (FIG. 3). In contrast to this, $alpha_v beta_3$-/$alpha_v beta_5$-negative control cells (M21L) do not show any significant cell adhesion. The cell adsorption rates described are raised about 20–40 fold compared with 5% BSA-coated surfaces which lead to no significant cell adhesion for all osteoblast cultures employed.

The similar behaviour of the osteoblast cultures mentioned confirms that the adhesion-stimulating effects are osteoblast-specific but species-independent.

Figure 4:
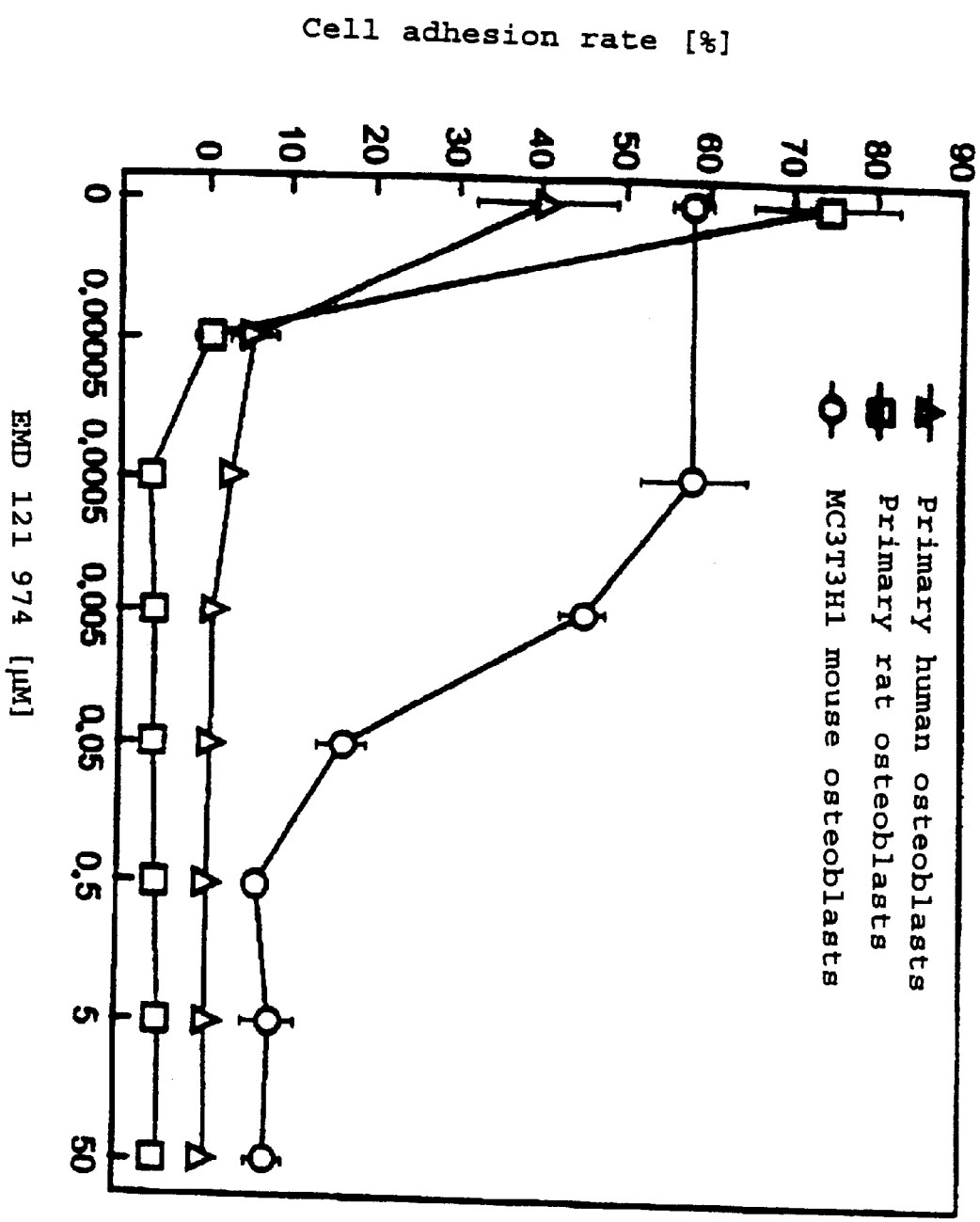

The binding of the abovementioned osteoblast cell cultures to BSA-pretreated polystyrene surfaces coated with thiolpeptide 1-sulpho-SMPB derivative can be completely inhibited by addition of dissolved cyclic RGDfK in the adhesion medium (FIG. 4). This result proves that the observed cell adhesion phenomena are mediated by RGD peptides alone.

Figure 7:
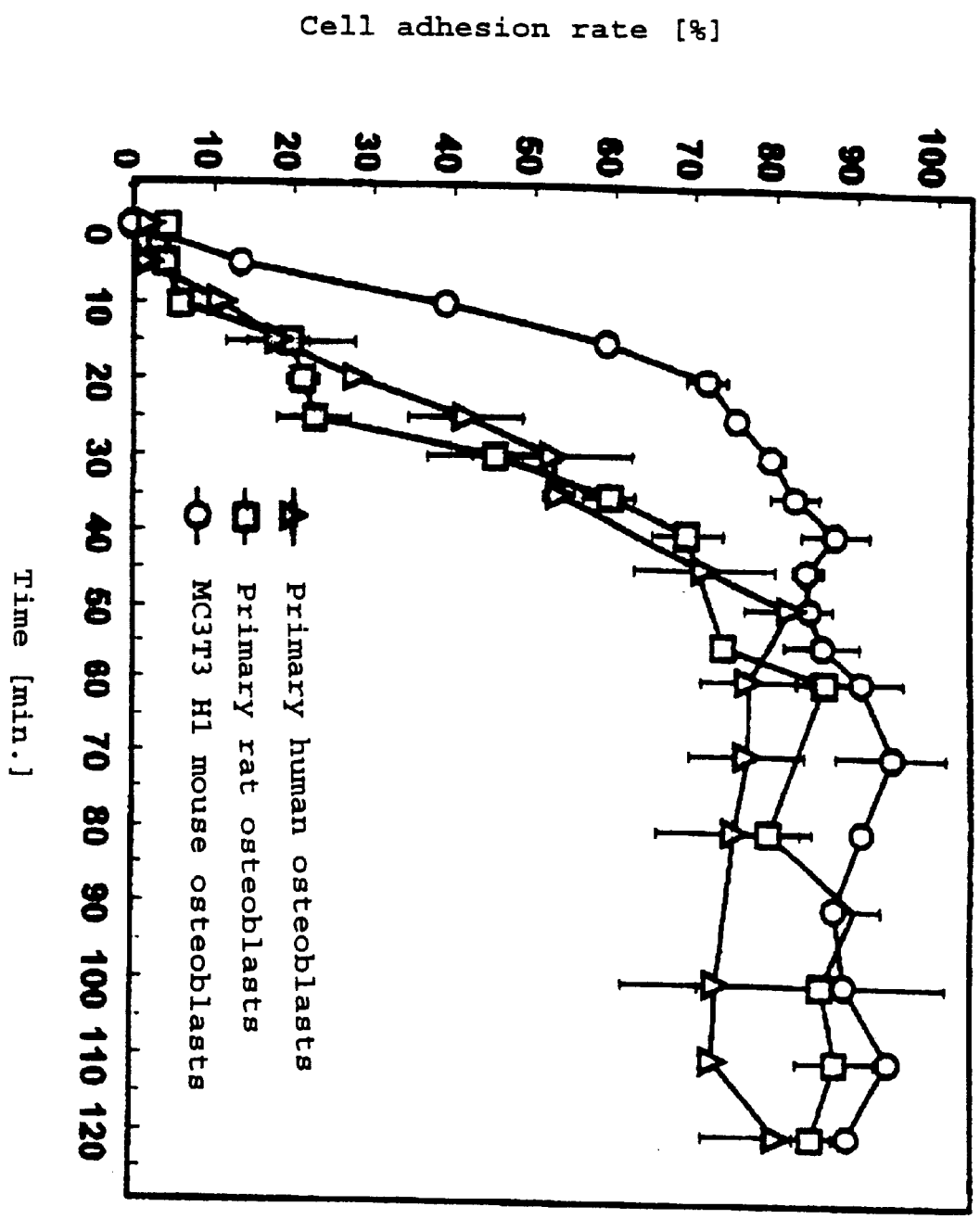

The dependence of the cell adhesion of primary human osteoblasts or of MC3T3 H1 cells on the mentioned thiolpeptide 1,2(sulpho-SMPB)-coated, BSA-pretreated polystyrene surfaces on the number of inoculated cells produces a saturation curve (FIG. 5). No significant cell adhesion can be discerned, however, on the BSA negative coating. The average surface area per adhered cell of about 200 to 500 $\mu m^2$ calculated in the case of maximal cell inoculation density produces on this surface an average cell-cell distance of approximately 15 to 25 µm (FIG. 6). Since the osteoblast cell diameter is about 10 to 15 µm, it is clear that the peptide coating makes available cell adhesion sites in a number such that a surface densely coated with osteoblasts can be achieved in which the cells are arranged in immediate proximity to one another. The time course of the cell adhesion process on the surface mentioned shows a rapid adhesion of the cells which, depending on the cell type, is complete after approximately 45 to 60 minutes (FIG. 7). Cell lines (e.g. MC3T3 H1) show more rapid adhesion kinetics here than primary cell cultures (human, rat). Significant differences between the two thiolpeptide derivatives used are not discernible in these experiments.

EXAMPLE 3

For the investigation of the effect of various anchor molecule lengths and thus of the distance between the cell-recognizing RGD sequence and the material surface on the extent of osteoblast adhesion, four different acrylate-RGD peptides (cyclo-RGDfK NH—CO-acrylate derivative (type: iia, iib, iiia, iiib) were prepared with different molecular spacer lengths.

The syntheses of cyclo-RGD peptides were carried out as indicated in Example 1 or corresponding to the processes of Pless et al., 1983, J. Biol. Chem. 258: 2340–2349 or of Gurrath et al., 1992, Eur. J. Biochem. 210: 911–921.

The corresponding anchor lengths of these peptides were approximately 2.6 nm (acrylate peptide 1, type iia), 3.5 nm (acrylate peptide 2, type iib), 3.7 nm (acrylate peptide 3, type iiia) and 4.2 nm (acrylate peptide 4, type iiib).

For the covalent coupling of these peptides to polymerized PMMA (polymethyl methacrylate) surfaces, appropriate shaped articles of differing porosity (diameter: 10 mm; height: 2 mm) were prepared from three different PMMA components.

Bone cement based on PMMA (Merck KGaA, Germany, Licence No. 5181.00.00) corresponding to the product description (40 g of powder+20 ml of liquid).

10 g of PMMA/PHEMA (polyhydroxyethyl methacrylate) granules, particle size 0.5–0.6 mm (Biomet) were mixed with 1.3 ml of an HEMA solution (68.6% HEMA, 29.4% TEGMA [triethylene glycol dimethacrylate], 2% tBPB, [tert-butyl peroxybenzoate]) and adhered by means of this to a porous support material.

10 g of PMMA granules (Plex Y7H, Röhm, Germany), particle fraction 0.7–2 mm were mixed with 1.5 ml of a methyl methacrylate (MMA) solution (68.6% MMA, 29.4% TEGMA, 2% tBPB) and adhered by this means to a porous support material.

For the covalent coupling of the acrylate peptides to the prepolymerized PMMA moulded articles, stock solutions of the acrylate peptides 1, 2, 3 and 4 were prepared in a final concentration of 100 $\mu$M in each case in DMSO/0.2% camphorquinone (w/v). Then, by dilution with isopropanol/0.2% camphorquinone (w/v), concentration series having final peptide concentrations of 0.1 nM, 1 nM, 10 nM, 100 nM, 1 $\mu$M and 10 $\mu$M in each case were prepared. The moulded articles were incubated in daylight and at room temperature for 2 hours and then stored at 4° C. in the dry state. Before use, the samples were washed with PBS, pH 7.4, to remove unbound peptides and stored at 4° C. in PBS, pH 7.4, overnight.

By addition of 250 $\mu$l/moulded article each of a 5% strength BSA solution in PBS, pH 7.4, and subsequent incubation for 2 hours at room temperature and washing once with PBS, pH 7.4, non-specific cell-binding sites were blocked.

PMMA moulded articles, which were treated with a solution of isopropanol/0.2% camphorquinone (w/v) instead of with the peptide solutions, functioned as negative controls.

Subsequently, the adhesion of osteoblasts of the MC3T3 H1 line, obtained from the calvaria of neonatal mice (Heermeier et al., 1995, Cells and Materials 5: 309–321) to the above-described peptide-coated surfaces was investigated.

The MC3T3 H1 osteoblasts were inoculated at an inoculation density of 48,000 cells/cm$^2$, as described above, in Costar 48-well plates, with PMMA moulded articles coated with RGD peptide and then incubated for 1 hour at 37° C., 95% atmospheric humidity and 5% $CO_2$. Cells non-adhered during the experiment were then washed off twice with PBS, pH 7.4.

The quantification of the adhered cells was carried out indirectly via the activity determination of the cellular enzyme N-acetylhexosaminidase using an appropriate standard curve according to the method of Landegren (1984, J. Immunol. Methods, 67: 379–388).

The binding behaviour of the MC3T3 H1 osteoblasts to different PMMA moulded articles coated with mentioned acrylate RGD peptides 1 (type iia), 2 (type iib), 3 (type iiia) and 4 (type iiib) in each case corresponds to a titration curve. The maximal adsorption rates are about 20% for acrylate peptide 1 and about 80–100% for the acrylate peptides 2, 3 and 4. The half-maximal cell bindings take place at an RGD peptide concentration in the coating solution of about 1–10, 000 nM for the acrylate peptides 2, 3 and 4.

Figure 8:
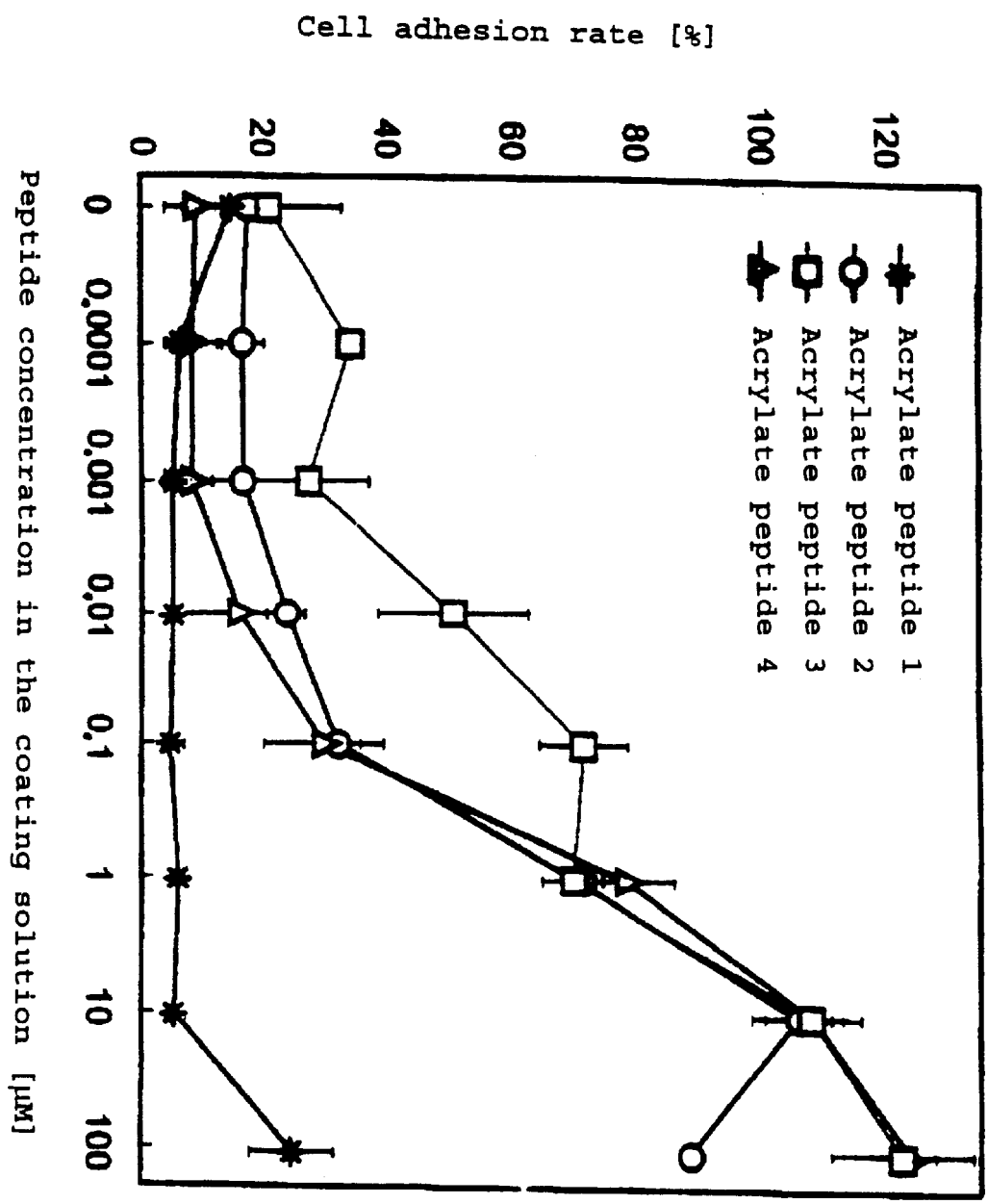

The described cell adsorption rates on RGD peptide-coated bone cement shaped articles are increased about 1.5 fold (acrylate peptide 1) and about 5–15 fold (acrylate peptides 2, 3 and 4) in comparison with uncoated surfaces (FIG. 8).

Figure 9:
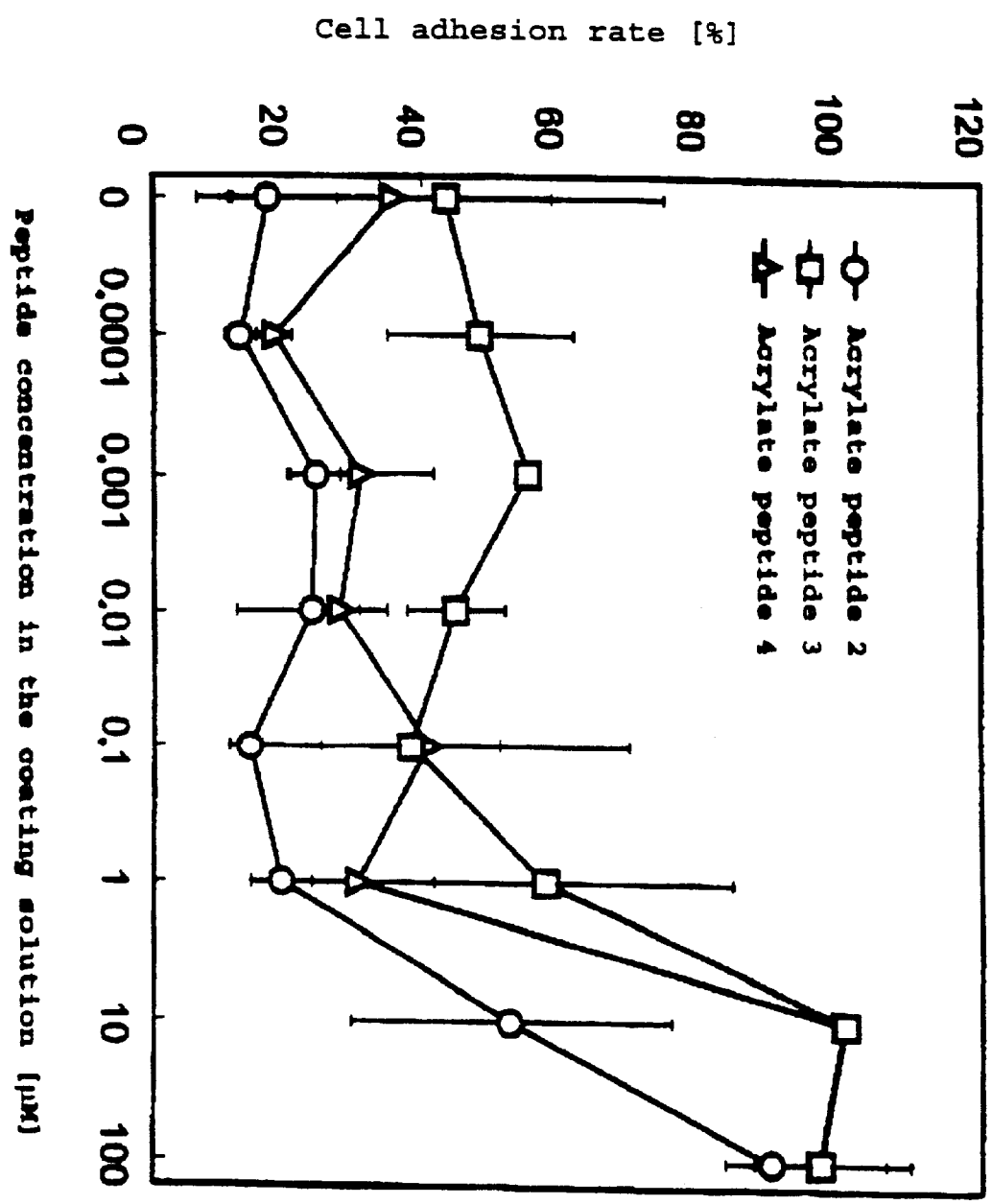

The described cell adsorption rates on RGD peptide-coated porous PMMA/PHEMA granule shaped articles are increased 2–5 fold (acrylate peptides 2, 3 and 4) in comparison with uncoated surfaces (FIG. 9).

Figure 10:
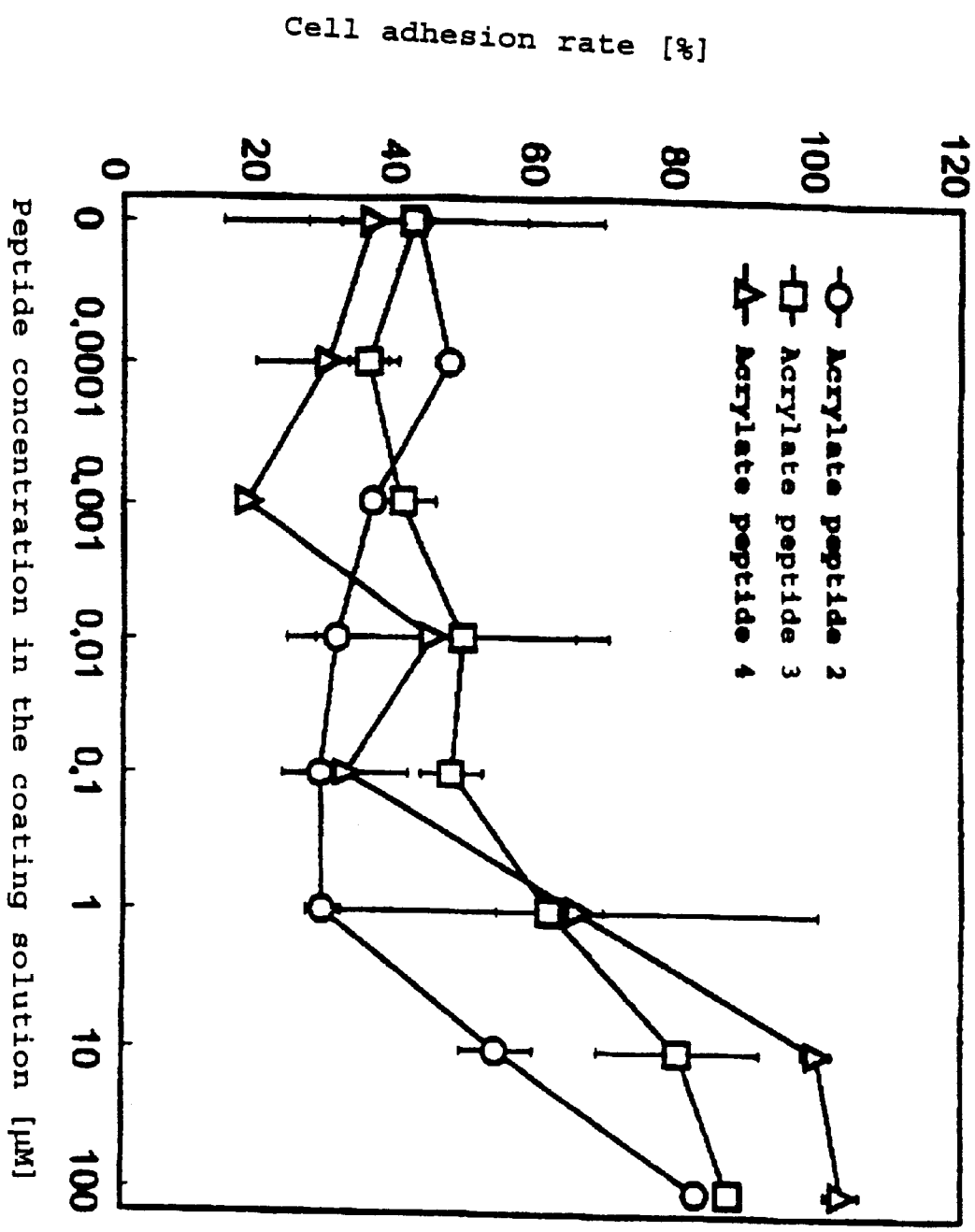

The described cell adsorption rates on RGD peptide-coated porous Plex Y7H granule shaped articles are increased 2–3 fold (acrylate peptides 2, 3 and 4) in comparison with uncoated surfaces (FIG. 10).

For PMMA/PHEMA or for PMMA-Plex Y7H samples, both a greater variation width of the cell adhesion values and a stronger adhesion of the osteoblasts to uncoated control samples with constant maximal adhesion rates to RGD peptide-coated samples are observed than for PMMA-bone cement shaped articles.

Figure 11:
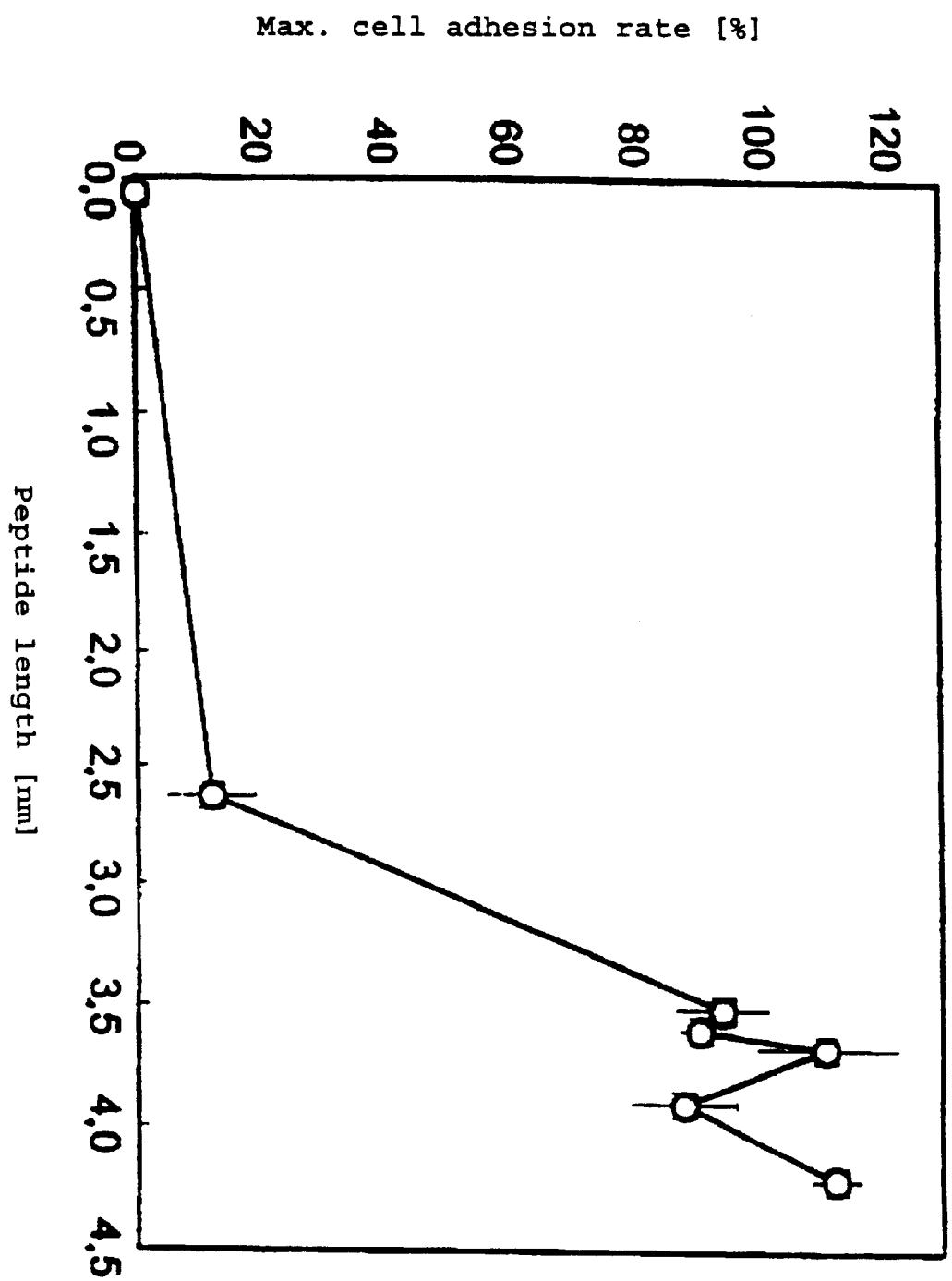

For the acrylate peptides 2, 3 and 4, both in comparison with one another and in comparison with the thiolpeptides 1 and 2 coated on the test BSA control, very similar stimulations of cell adhesion are observed, but the shortest peptide, acrylate peptide 1, is almost inactive. It can be concluded from this that a critical minimum distance of about 2.5–3.5 nm is necessary between RGD cell recognition sequence and the material surface in order to be able to carry out sterically successful cell adhesion (FIG. 11).

The higher activity of acrylate peptide 3 on the bone cement-PMMA carrier points to a molecular structure optimal for cell adhesion with respect to both the molecule length and optionally the hydrophilic/hydrophobic distribution or ratio in the spacer.

EXAMPLE 4

For testing the cell adhesion of osteoblasts to peptide-coated metal surfaces, V4A stainless steel shaped articles (7×7×1 mm$^3$) were provided with three different coating variants and in each case then coated in turn with RGD peptides. To do this, first the stainless steel shaped articles were incubated in an ultrasonic bath at 60° C. for 15 min for the purpose of cleaning, rinsed with demineralized water, incubated in acetone for 30 min, rinsed again with demineralized water and incubated at 60° C. for 24 hours for drying.

The stainless steel platelets were then coated by means of three variants:

a. Kevloc® Process (Heraeus Kulzer GmbH, Wehrheim, Germany)

The Kevloc® primer solution was thinly applied and incubated at room temperature for 3 min. Then the Kevloc® bond solution was likewise thinly applied and activated in a kiln at 180° C. for 20 min.

Since this coating variant directly makes available free acrylate radicals on the metal surface, it was then possible to directly covalently couple the acrylate peptide 3, types iiia, as was described in Example 3 for polymerized PMMA-bone cement.

b. Silicoater® Process (Heraeus Kulzer GmbH, Wehrheim, Germany)

The Siliseal® solution was thinly applied and dried at room temperature for 5 min. Then the Sililink solution was likewise thinly applied and activated in the kiln at 320° C. for 3 min.

To make available acrylate radicals on the coated metal surfaces, the pretreated stainless steel shaped articles were immersed in demineralized water heated to 75° C., adjusted to pH about 8.00 using NaOH. A 1% 3-methacryloxypropyltrimethoxysilane solution (Hüls AG, Germany) was then metered in with stirring over a period of one hour until a pH of about 6.50 was achieved. The mixture was then stirred at 75° C. for one hour; the pH at this time was about 6.35.

The bonding of acrylate peptide 3, type iiia, was carried out as described in Example 3 for polymerized PMMA bone cement.

c. Pigment Coating (Merck KGBA, Darmstadt, Germany)

This coating variant was carried out according to a silanization process which is described in DE-A 4321005, and which originally represents the technical teaching of the coating of pearl lustre pigments for water-based coating systems for metals and plastics in the automotive and plastics industry.

For this, the stainless steel shaped articles were immersed in demineralized water heated to 75° C., adjusted to pH about 8.00 using NaOH, and an $AlCl_3$ solution was metered in with stirring over a period of two hours. Then a 5% sodium silicate solution was likewise metered in with stirring over two hours. In the following step, a 1% 3-methacryloxypropyltrimethoxysilane solution (Hüls AG, Germany) was metered in with stirring in the course of one hour. The mixture was then stirred at 75° C. for one hour; the pH was at this time about 6.40.

The bonding of acrylate peptide 3, type iiia, was carried out as described in Example 3 for polymerized PMMA bone cement.

After the stainless steel shaped articles had been coated with acrylate peptide 3, type iiia, by means of three different processes, the adhesion of osteoblasts of the line MC3T3 H1 was investigated. To do this, a procedure as described in Example 3 was used.

The binding behaviour of the MC3T3 H1 osteoblasts to V4A stainless steel shaped articles coated with the said acrylate peptide 3 and pretreated using three different processes in each case corresponds to a titration curve (FIG. 12).

The maximum adhesion rates were about 60% for the pigment coating and about 80% for Kevloc® or Silicoater® processes. The half-maximal cell bindings take place at an RGD peptide concentration in the coating solution of about 1–100 nM for all three coating variants. The described cell absorption rates on PGD peptide-coated stainless steel shaped articles are increased about 3- to 8-fold compared with uncoated controls.

For Kevloc® or Silicoater® processes, in each case coatings were additionally produced using only one costing solution (Kevloc® primer alone, Kevloc® bond alone, Siliseal® alone, Sililink® alone). In this case no significant differences in the cell adhesion in comparison with the respective double coatings (Kevloc® primer/bond, Siliseal®/Sililink®) were observed.

EXAMPLE 5

For the supplementary investigation of not only osteoblast adhesion, but also their proliferation on RGD peptide-coated surfaces, the procedure was as follows:

For the covalent coupling of acrylate peptide 3, type iiia, to polymerized PMMA bone cement shaped articles, a coating process which was described in Example 3 was selected.

MC3T3 H1 mouse osteoblasts were then adhered to these RGD peptide-coated bone cement shaped articles as likewise described in Example 3, but with two differences: 12,000 cells/cm² instead of 48,000 cells/cm² were inoculated and the adhesion time was two hours instead of one hour. Additionally, only three different peptide concentrations were investigated in the coating solution: 0.01 $\mu$M, 1 $\mu$M and 100 $\mu$M.

After washing off non-adherent cells, the MC3T3 H1 osteoblasts were cultured under 95% atmospheric humidity and 5% $CO_2$ at 37° C. in serum-containing (10%) culture medium for a period of 15 days. During the course of this, the medium was changed twice per week and after 1, 2, 3, 4, 5, 10 and 15 days the cell count was determined by means of the WST-1 test by Boehringer Mannheim, Germany. In each case a typical exponential course of the cell proliferation of the cultured osteoblasts was seen here (FIG. 13). The maximally achieved cell count was directly dependent on the RGD peptide concentration in the coating solution. Thus after 15 culturing days per cm², about 1,000,000 cells (100 $\mu$M peptide), about 550,000 cells (1 $\mu$M peptide), about 300,000 cells (0.01 $\mu$M peptide) or about 230,000 cells were achieved (control without peptide). At the highest peptide concentration of 100 $\mu$M, an approximately 4- to 5-fold increase in the cell proliferation in comparison with uncoated samples was thus observed.

EXAMPLE 6

The model used for material coating with RGD peptides of different cell selectivity to obtain implants having locally differentiated bioactive coating patterns which should stimulate the adhesion of different cell species was polymerized PMMA bone cement shaped articles. To these were covalently coupled two RGD peptides of different cell selectivity. In this case acrylate peptide 3, type iiia, having a selectivity for $alpha_v beta_3$-/$alpha_v beta_5$-integrin-bearing osteoblasts, and acrylate peptide 5, type iiia, having a selectivity for $alpha_{IIb} beta_3$-positive platelets were bonded to the PMMA shaped articles as described for Example 3.

a. In the first part experiment, PMMA shaped articles were coated with the acrylate peptides 3 and 5 in concentrations in the coating solution of 100 $\mu$M, 10 $\mu$M and 1 $\mu$M in each case. These RGD peptide-coated materials were then inoculated in parallel with osteoblasts and platelets and their cell adhesion was determined.

MC3T3 H1 osteoblasts (350,000 cells/cm²) and human platelets (50 million cells/cm²) were in each case inoculated in parallel both onto acrylate peptide 3- and acrylate peptide 5-coated PMMA shaped articles and their cell adhesion was determined as described in Example 3.

Human platelets were prepared following the process of Shattil and Brass (J. Biol. Chem. 262:992–1000, 1987). It was possible to demonstrate the cell selectivity of the two RGD peptides using this experiment.

$Alpha_v beta_3$-/$alpha_v beta_5$-positive osteoblasts adhered peferably to acrylate peptide 3 ($alpha_v beta_3$-/$alpha_v beta_5$-selective)-coated PMMA shaped articles in comparison to $alpha_v beta_3$-/$alpha_v beta5$-negative platelets (FIG. 14). Calculated Abs (405 nm) of about 6.0 (for 100 $\mu$M peptide in the coating solution), about 2.0 (for 10 $\mu$M peptide) or about 1.8. (for 1 $\mu$M peptide) were found here for osteoblasts. For platelets, however, significantly lower cell adhesion values of about 3.0 Abs (for 100 $\mu$M peptide in the coating solution), about 1.5 Abs (for 10 $\mu$M peptide) or about 0.2 Abs (for 1 $\mu$M peptide) were found. A converse effect was found, however, on acrylate peptide 5 ($alpha_{IIb} beta_3$-selective)-coated PMMA shaped articles. In this case, $alpha_{IIb} beta_3$-positive platelets adhered preferably in comparison to $alpha_{IIb} beta_3$-negative osteoblasts (FIG. 15).

Calculated Abs (405 nm) of about 4.0 (for 100 $\mu$M peptide in the coating solution), about 0.5 (for 10 $\mu$M peptide) or about 0.2 (for 1 $\mu$M peptide) were found here for platelets. For osteoblasts, however, significantly lower cell adhesion values of about 1.5 Abs (for 100 $\mu$M peptide in the coating solution), about 1.0 Abs (for 10 $\mu$M peptide) or about 0.2 Abs (for 1 $\mu$M peptide) were found.

b. In the second part experiment, PMMA shaped articles were likewise coated with the acrylate peptides 3 and 5, but only in a concentration in the coating solution of 100 μM in each case. These RGD peptide-coated materials were then inoculated in parallel with osteoblasts, platelets or an osteoblast/platelet mixture and their cell adhesion was determined. MC3T3 H1 osteoblasts (350,000 cells/cm$^2$), human platelets (50 million cell/cm$^2$) and a cell mixture (350,000 osteoblasts/cm$^2$ or 50 million platelets/cm$^2$) were in each case inoculated in parallel both onto acrylate peptide 3- and acrylate peptide 5-coated PMMA shaped articles and their cell adhesion was determined as described in Example 3.

Alpha$_v$beta$_3$-/alpha$_v$beta$_5$-positive osteoblasts (about 6.0 Abs) adhered preferably to acrylate peptide 3-coated PMMA shaped articles in comparison to alpha$_v$beta$_3$-/alpha$_v$beta5-negative platelets (about 3.0 Abs) (FIG. 16). If both cell species were inoculated as a mixture, a result was obtained which corresponds to that of osteoblasts alone (about 6.5 Abs).

A converse effect, however, was found on acrylate peptide 5 (alpha$_{IIb}$beta$_3$-selective)-coated PMMA shaped articles. alpha$_{IIb}$beta$_3$-positive platelets (about 4.0 Abs) adhered preferably here in comparison to alpha$_{IIb}$beta$_3$-negative osteoblasts (about 1.5 Abs) (FIG. 17). If both cell species were inoculated as a mixture, a result was obtained which corresponds approximately to the sum of the individual values for platelets and osteoblasts (about 6.5 Abs).

These results confirm that the coatings of implant surfaces with various cell-selective RGD peptides can be used for the generation of implants which mediate the preferred adhesion of selected cell species. In this case, the comparison between osteoblasts and platelets shows that the surface coating with integrin-selective RGD peptides can markedly stimulate the adhesion of those cell species which have a complementary integrin make-up compared with cells which do not have these special integrins or only have them to a small extent.

this effect remains even when using cell mixtures, which comes significantly closer to the in vivo state.

What is claimed is:

1. An implant suitable for a human or animal organ, comprising a carrier matrix and a peptide coating surrounding this matrix which contains different peptides for the targeted adhesion stimulation of human or animal body cells, wherein said peptides have a length of 3 to 20 amino acids and comprise sequences which recognize binding sites on integrin receptors responsible for adhesion on said human or animal cells, the carrier matrix has, bound to its surface reactive groups capable of entering into a stable covalent bond with functional reactive groups of said peptides or of anchor molecules for attaching said peptides to the carrier matrix surface, and said peptides are arranged of the surface of the implant such that their different structure-related, cell adhesion-stimulating activities correspond specifically to the natural different complementary integrin pattern of said human or animal cells in the particular region into which the implant is to be inserted, thereby forming a locally differentiated, selective, bioactive coating pattern on the implant surface.

2. The implant according to claim 1, wherein said peptides are attached to the surface of the implant with the aid of anchor molecules.

3. The implant according to claim 2, wherein the anchor molecules consist of one of the following structures:

$$-CO-(CH_2)_k-X-SH, \quad (i)$$

where X is a single bond or $-CO-NH-(CH_2)_l-$, k=2 to 12 and l=2 to 4;

$$-CO-(CH_2)_m-[NH-CO-(CH_2)_n]_p-NH-CO-CH=CH_2 \quad (ii)$$

where m,n=2 to 8; p=0 to 2, $$-(CO-CH_2-O-CH_2-CH_2-O-CH_2-CH_2-NH)_q-CO-$$

$(CH_2)_r$—NH—CO—CH=$CH_2$ (iii)

where q=1 to 3 and r=2 to 8.

4. The implant according to claim 3, wherein the anchor molecules are selected from one of the following structures:

—CO—$CH_2$—$CH_2$—SH; (ia)

—CO—$CH_2$—$CH_2$—CO—NH—$CH_2$—$CH_2$—SH; (ib)

—CO—$(CH_2)_5$—NH—CO—CH=$CH_2$; (iia)

—CO—$(CH_2)_5$—NH—CO—$(CH_2)_5$—NH—CO—CH=$CH_2$; (iib)

—CO—$CH_2$—O—$CH_2$—$CH_2$—O—$CH_2$—$CH_2$—NH—CO—$(CH_2)_5$—NH—CO—CH=$CH_2$; (iiia)

—(CO—$CH_2$—O—$CH_2$—$CH_2$—O—$CH_2$—$CH_2$—NH)$_2$—CO—$(CH_2)_5$—NH—CO—CH=$CH_2$ (iiib).

5. The implant according to claim 3, wherein the peptides are bonded to the anchor molecules by amide bonding with the —CO— group of the anchor molecules, and the anchor molecules are bonded to the implant surface via mercapto or acrylate group(s).

6. The implant according to claim 5, wherein the anchor molecule is attached to the implant surface such that a sterically critical, absolute minimum distance between the sequences of the peptide which recognize binding sites on the integrin receptors and the carrier matrix in its uncoated form, is 2.5 to 3.5 nm.

7. The implant according to claim 1 wherein the peptides are able to bind to $\alpha_v\beta_3$-/$\alpha_v\beta_5$-expressing cells.

8. The implant according to claim 1, wherein one or more of the peptides comprise the amino acid sequence RGD.

9. The implant according to claim 8, wherein one or more of the peptides comprise the sequence cyclo-RGDfK or cyclo-RGDfKG.

10. The implant according to claim 1, which contains an adhesion-promoting intermediate layer, and/or branched molecules which bring about a surface-enlarging effect, between said peptides, or peptides which are bonded to anchor molecules, and the surface of the carrier matrix.

11. The implant according to claim 1, wherein the carrier matrix is an appropriately shaped piece of ceramic, polymer material, or metal, or is a biohybrid organ, made by colonizing said shaped piece in vivo or in vitro with cells.

12. A process for the preparation of an implant according to claim 1, comprising (i) determining by means of an in vitro test system the integrin pattern of the region into which the implant is to be inserted in vivo, (ii) selecting or synthesizing said peptides which correspond to said integrins and, (iii) covalently binding said peptides to the surface of the implant directly or via anchor molecules, the local arrangement of different peptides on the surface of the implant corresponding to the particular previously determined complementary integrin pattern of the region into which the implant is to be inserted.

13. The process according to claim 12, wherein the in vitro determination of said integrin pattern is carried out by means of immunohistologically active antibodies.

14. The process according to claim 12, wherein the covalent binding of said peptides, or of peptides bonded to anchor molecules, to the implant surface is carried out by means of processes known for other types of coating.

15. The implant according to claim 2, wherein the anchor molecules have a mercapto or an acrylate group at one terminus and a —CO— group at the other terminus; the peptides are bonded to the anchor molecules by amide bonding with the —CO— group of the anchor molecules; and the anchor molecules are bonded to the implant surface via the mercapto or acrylate groups.

16. The implant according to claim 4, wherein the peptides are bonded to the anchor molecules by amide bonding with the —CO— group of the anchor molecules, and the anchor molecules are bonded to the implant surface via the mercapto or acrylate group(s).

17. The implant according to claim 1, wherein one or more of said peptides comprise the sequence LDV, LRE, or the sequence of SEQ ID NOS: 1–13.

18. The implant according to claim 2, wherein said anchor molecules comprise a linear carbon chain comprising at least 6 carbons.

19. The implant according to claim 18, wherein said anchor molecules comprise a linear carbon chain of 6 to 24 C atoms.

20. The implant according to claim 2, wherein the implant comprises a structure wherein the peptide cyclo-RGDfK NH—CO is attached via an amide bond to an anchor which comprises 6 to 24 C atoms and has at the end which is bonded to the implant surface a mercapto group, an acrylate group, or an acrylate-glycol group, or the peptide cyclo-RGDfKG NH—CO is attached via an amide bond to an anchor which comprises 6 to 24 C atoms and has at the end which is bonded to the implant surface an acrylate-glycol group.

21. The implant according to claim 19, wherein the implant comprises a structure wherein the peptide cyclo-RGDfK NH—CO is attached via an amide bond to an anchor which comprises 6 to 24 C atoms and has at the end which is bonded to the implant surface a —CO—$CH_2$—$CH_2$—CO—NH—$CH_2$—$CH_2$—SH group, a —CO—$(CH_2)_5$—NH—CO—CH=$CH_2$ group, a —CO—$(CH_2)_5$—NH—CO—$(CH_2)_5$—NH—CO—CH=$CH_2$ group, a —CO—$CH_2$—O—$CH_2$—$CH_2$—O—$CH_2$—$CH_2$—NH—CO—$(CH_2)_5$—NH—CO—CH=$CH_2$ group, or a —(CO—$CH_2$—O—$CH_2$—$CH_2$—O—$CH_2$—$CH_2$—NH)$_2$—CO—$(CH_2)_5$—NH—CO—CH=$CH_2$, or the peptide cyclo-RGDfKG NH—CO is attached via an amide bond to an anchor which comprises 6 to 24 C atoms and has at the end which is bonded to the implant surface a —CO—$CH_2$—O—$CH_2$—$CH_2$—O—$CH_2$—$CH_2$—NH—CO—$(CH_2)_5$—NH—CO—CH=$CH_2$ group.

* * * * *

```
                         SEQUENCE LISTING

<160> NUMBER OF SEQ ID NOS:  13

<210> SEQ ID NO 1
   <211> LENGTH: 4
   <212> TYPE: PRT
   <213> ORGANISM: Artificial Sequence
   <220> FEATURE:
   <223> OTHER INFORMATION: Description of Artificial Sequence: Suitable
         RGD-containing peptide

<400> SEQUENCE: 1

Gly Arg Gly Asp
     1

<210> SEQ ID NO 2
   <211> LENGTH: 5
   <212> TYPE: PRT
   <213> ORGANISM: Artificial Sequence
   <220> FEATURE:
   <223> OTHER INFORMATION: Description of Artificial Sequence: Suitable
         RGD-containing peptide

<400> SEQUENCE: 2

Gly Arg Gly Asp Tyr
     1               5

<210> SEQ ID NO 3
   <211> LENGTH: 4
   <212> TYPE: PRT
   <213> ORGANISM: Artificial Sequence
   <220> FEATURE:
   <223> OTHER INFORMATION: Description of Artificial Sequence: Suitable
         RGD-containing peptide

<400> SEQUENCE: 3

Arg Gly Asp Ser
     1

<210> SEQ ID NO 4
   <211> LENGTH: 5
   <212> TYPE: PRT
   <213> ORGANISM: Artificial Sequence
   <220> FEATURE:
   <223> OTHER INFORMATION: Description of Artificial Sequence: Suitable
```

```
        RGD-containing peptide

<400> SEQUENCE: 4

Gly Arg Gly Asp Ser
 1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Suitable
      RGD-containing peptide

<400> SEQUENCE: 5

Arg Gly Asp Phe
 1

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Suitable
      RGD-containing peptide

<400> SEQUENCE: 6

Gly Arg Gly Asp Phe
 1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Suitable
      non-RGD-containing peptide

<400> SEQUENCE: 7

Leu Gly Thr Ile Pro Gly
 1               5

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Suitable
      non-RGD-containing peptide

<400> SEQUENCE: 8

Arg Glu Asp Val
 1

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Suitable
      non-RGD-containing peptide

<400> SEQUENCE: 9

Ile Lys Val Ala Val
 1               5

<210> SEQ ID NO 10
```

```
<211> LENGTH: 6
<212> TYPE: PRT
<213> ORGANISM: Artificial Sequence
<220> FEATURE:
<223> OTHER INFORMATION: Description of Artificial Sequence: Suitable
      non-RGD-containing peptide

<400> SEQUENCE: 10

Tyr Ile Gly Ser Arg Gly
  1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Suitable
      non-RGD-containing peptide

<400> SEQUENCE: 11

Pro Asp Ser Gly Arg
  1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Suitable
      non-RGD-containing peptide

<400> SEQUENCE: 12

Asp Gly Glu Ala
  1

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Suitable
      non-RGD-containing peptide

<400> SEQUENCE: 13

Arg Tyr Val Val Leu Pro Arg
  1               5
```